US009290381B2

(12) United States Patent
Nair et al.

(10) Patent No.: US 9,290,381 B2
(45) Date of Patent: Mar. 22, 2016

(54) FUNCTIONALIZED SINGLE-WALLED NANOTUBES AND METHODS THEREOF

(71) Applicant: Georgia Tech Research Corporation, Atlanta, GA (US)

(72) Inventors: Sankar Nair, Atlanta, GA (US); Dun-Yen Kang, Atlanta, GA (US); Nicholas A. Brunelli, Atlanta, GA (US); Christopher W. Jones, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/482,552

(22) Filed: Sep. 10, 2014

(65) Prior Publication Data
US 2015/0087852 A1 Mar. 26, 2015

Related U.S. Application Data

(60) Provisional application No. 61/882,910, filed on Sep. 26, 2013.

(51) Int. Cl.
*B82Y 10/00* (2011.01)
*C07F 7/08* (2006.01)
*C07F 7/18* (2006.01)

(52) U.S. Cl.
CPC ............... *B82Y 10/00* (2013.01); *C07F 7/0854* (2013.01); *C07F 7/1828* (2013.01); *C07F 7/1836* (2013.01)

(58) Field of Classification Search
CPC .................................. C07F 7/1804; C07F 7/10
See application file for complete search history.

(56) References Cited

U.S. PATENT DOCUMENTS

| | | | |
|---|---|---|---|
| 4,874,518 A | 10/1989 | Kirkland et al. | |
| 2002/0090330 A1 | 7/2002 | Smalley et al. | |
| 2003/0026754 A1 | 2/2003 | Clarke et al. | |
| 2004/0048744 A1 | 3/2004 | Iijima et al. | |
| 2008/0213487 A1 | 9/2008 | Park et al. | |
| 2010/0117032 A1 | 5/2010 | Grigorian et al. | |
| 2010/0224555 A1 | 9/2010 | Hoek et al. | |
| 2011/0230672 A1* | 9/2011 | Kang et al. | 556/173 |

FOREIGN PATENT DOCUMENTS

| | | |
|---|---|---|
| JP | 5701373 B2 | 2/2015 |
| KR | 10-1427222 B1 | 7/2014 |

OTHER PUBLICATIONS

Barron, et al., *Detection of imogolite in soils using solid state $^{29}Si$ NMR*, Nature 299(5884) (Oct. 14, 1982) 616-618.
Bollini, et al., *Amine-oxide hybrid materials for acid gas separations*, J. Mater. Chem. 21(39) (Oct. 21, 2011) 15100-15120.
Bollini, et al., *Oxidative degradation of aminosilica adsorbents relevant to postcombustion $CO_2$ capture*, Energy Fuels 25 (2011) 2416-2425.
Bottero, et al., *Synthesis and characterization of hybrid organic/inorganic nanotubes of the imogolite type and their behavior towards methane adsorption*, Phys. Chem. Chem. Phys. 13(2) (Jan. 14, 2011) 744-750.
Brunelli, et al., *Tuning cooperativity by controlling the linker length of silica-supported amines in catalysis and $CO_2$ capture*, J. Am. Chem. Soc. 134 (2012) 13950-13953.
Cambedouzou, et al., *On the diffraction pattern of $C_{60}$ peapods*, Eur. Phys. J. B 42 (2004) 31-45.
Choi, et al., *Adsorbent materials for carbon dioxide capture from large anthropogenic point sources*, ChemSusChem 2 (2009) 796-854.
Ek, et al., *A $^{29}Si$ and $^{13}C$ CP/MAS NMR study on the surface species of gas-phase-deposited delta-aminopropylalkoxysilanes on heat-treated silica*, J. Phys. Chem. B 108(31) (2004) 11454-11459.
Giambastiani, et al., *Functionalization of multiwalled carbon nanotubes with cyclic nitrones for materials and composites: Addressing the role of CNT sidewall defects*, Chem. Mater. 23 (2011) 1923-1938.
Grey, et al., *Determination of the quadrupole coupling constant of the invisible aluminum spins in zeolite HY with $^1H/^{27}Al$ TRAPDOR NMR*, J. Am. Chem. Soc. 117(31) (Aug. 9, 1995) 8232-8242.
Hoffmann, et al., *Silica-based mesoporous organic-inorganic hybrid materials*, Angew. Chem. Int. Ed. 45(20) (May 4, 2006) 3216-3251.
Holland, et al., *Location and orientation of adsorbed molecules in zeolites from solid-state REAPDOR NMR*, Phys. Chem. Chem. Phys. 7(8) (Apr. 21, 2005) 1739-1742.
Iijima, *Helical microtubules of graphitic carbon*, Nature 354(6348) (Nov. 7, 1991) 56-58.
Jones, et al., *Organic-functionalized molecular sieves as shape-selective catalysts*, Nature 393 (May 7, 1998) 52-54.
Jones, et al., *Organic-functionalized molecular sieves (OFMSs): II. Synthesis, characterization and the transformation of OFMSs containing non-polar functional groups into solid acids*, Microporous Mesoporous Mater. 33(1-3) (Dec. 15, 1999) 223-240.
Kang, et al., *Single-walled aluminosilicate nanotubes with organic-modified interiors*, J. Phys. Chem. C 115 (2011) 7676-7685.
Kang, et al., *Single-walled aluminosilicate nanotube/poly(vinyl alcohol) nanocomposite membranes*, ACS Appl. Mater. Interfaces 4 (2012) 965-976.
Karousis, et al., *Current progress on the chemical modification of carbon nanotubes*, Chem. Rev. 110(9) (2010) 5366-5397.
Kuzmany, et al., *Functionalization of carbon nanotubes*, Synth. Met. 141 (2004) 113-122.

(Continued)

*Primary Examiner* — Sudhakar Katakam
(74) *Attorney, Agent, or Firm* — Gardere Wynne Sewell LLP; Chris P. Perque; Teresa J. Lechner-Fish

(57) ABSTRACT

Described are single-walled metal oxide nanotubes having a plurality of organic functional units or moieties bonded generally in a covalent manner to the inner wall of the single-walled nanotubes. Functionalization of the single-walled metal oxide nanotubes is performed in a single-step during synthesis of the nanotubes. The organic functional units are found dispersed throughout the length of the inner wall and not sterically hindered or contained at only the mouth or ends of the single-walled metal oxide nanotubes.

20 Claims, 11 Drawing Sheets
(11 of 11 Drawing Sheet(s) Filed in Color)

(56) References Cited

OTHER PUBLICATIONS

Levard, et al., *Formation and growth mechanisms of imogolite-like aluminogermanate nanotubes*, Chem. Mater. 22(8) (2010) 2466-2473.
Ma, et al., *Dispersion and functionalization of carbon nanotubes for polymer-based nanocomposites: A review*, Composites: Part A 41 (2010) 1345-1367.
Maillet, et al., *Growth kinetic of single and double-walled aluminogermanate imogolite-like nanotubes: An experimental and modeling approach*, Phys. Chem. Chem. Phys. 13(7) (Feb. 21, 2011) 2682-2689.
Majumder, et al., *Mass transport through carbon nanotube membranes in three different regimes: Ionic diffusion and gas and liquid flow*, ACS Nano 5(5) (2011) 3867-3877.
Mukherjee, et al., *Short, highly ordered, single-walled mixed-oxide nanotubes assemble from amorphous nanoparticles*, J. Am. Chem. Soc. 129(21) (May 30, 2007) 6820-6826.
Singh, et al., *Carbon nanotube surface science*, Int. J. Nanotechnol. 5(9-12) (2008) 900-929 (Invited Review).
Singh, et al., *Organic functionalisation and characterisation of single-walled carbon nanotubes*, Chem. Soc. Rev. 38 (2009) 2214-2230.
Stein, et al., *Hybrid inorganic-organic mesoporous silicates—nanoscopic reactors coming of age*, Adv. Mater. 12(19) (Oct. 2, 2000) 1403-1419.
Tagliabue, et al., *Natural gas treating by selective adsorption: Material science and chemical engineering interplay*, Chem. Eng. J. 155 (2009) 553-566.
Theng, et al., *Surface properties of allophane, halloysite, and imogolite*, Clays & Clay Minerals 30(2) (1982) 143-149.
Tsuji, et al., *Organic-functionalized molecular sieves (OFMSs) I. Synthesis and characterization of OFMSs with polar functional groups*, Microporous Mesoporous Mater. 29(3) (1999) 339-349.
Vairavapandian, et al., *Preparation and modification of carbon nanotubes: Review of recent advances and applications in catalysis and sensing*, Anal. Chim. Acta 626 (2008) 119-129.
Venkatasubramanian, et al., *Gas adsorption characteristics of metal-organic frameworks via quartz crystal microbalance techniques*, J. Phys. Chem. C 116 (2012) 15313-15321.
Wada, et al., *Synthetic allophane and imogolite*, J. Soil Sci. 30 (1979) 347-355.
Yanagi, et al., *Photosensitive function of encapsulated dye in carbon nanotubes*, J. Am. Chem. Soc. 129(16) (Apr. 25, 2007) 4992-4997.
Yucelen, et al., *Shaping single-walled metal oxide nanotubes from precursors of controlled curvature*, Nano Lett. 12 (2012) 827-832.
Zanzottera, et al., *Physico-chemical properties of imogolite nanotubes functionalized on both external and internal surfaces*, J. Phys. Chem. C 116 (2012) 7499-7506.
PCT Jun. 16, 2011 International Search Report and Written Opinion issued for International Patent Application PCT/US2011/028649.
Li, et al., *The electronic structure of a single-walled aluminosilicate nanotube*, Nanotechnology 19(17) (2008) 1-9.
Yuan, et al., *Functionalization of halloysite clay nanotubes by grafting with gamma-aminopropyltriethoxysilane*, J. Phys. Chem. C 112 (2008) 15742-15751.
Zheng, *Syntheis and modifications of metal oxide nanostructures and their applications*, Queensland University of Technology School of Physical and Chemical Sciences Inorganic Materials Research Group (1999).
PCT Sep. 25, 2012 International Preliminary Report on Patentability issued for International Patent Application PCT/US2011/028649.
Yang, et al., *Growth mechanism of synthetic imogolite nanotubes*, Chem. Mater. 20(13) (2008) 4484-4488.
Yamamato, *Transparent polymer nanohybrid prepared by in situ synthesis of aluminosilicate nanofibers in poly(vinyl alcohol) solution*, Soft Matter (2005), 372-377.
Yucelen, *Formation of single-walled aluminosilicate nanotubes from molecular precursors and curved nanoscale intermediates*, J. Am. Chem. Soc. 133 (2011) 5397-5412.
Zang, *Flexibility of ordered surface hydroxyls influences the adsorptioin of molecules in single-walled aluminosilicate nanotubes*, J. Phys. Chem. Lett. 1 (2010) 1235-1240.

Bac, et al., *Surface-modified aluminogermanate nanotube by OPA: Synthesis and characterization*, Inorganic Chem. Comm. 12(10) (Oct. 2009) 1045-1048.
Farmer, et al., *Synthesis of imogolite: a tubular aluminum silicate polymer*, J. Chem. Soc. Chem. Comm. 13 (1977) 462-463.
Kang, et al., *Dehydration, dehydroxylation, and rehydroxylation of single-walled aluminosilicate nanotubes*, ACS Nano 4(8) (2010) 4897-4907.
Kang, et al., *Modeling molecular transport in composite membranes with tubular fillers*, J. Membr. Sci. 381 (2011) 50-63.
Konduri, et al., *Controlling nanotube dimensions: Correlation between composition, diameter, and internal energy of single-walled mixed oxide nanotubes*, ACS Nano 1(5) (2007) 393-402.
Konduri, et al., *Water in single-walled aluminosilicate nanotubes: Diffusion and adsorption properties*, J. Phys. Chem. C 112(39) (Oct. 2, 2008) 15367-15374.
Ma, et al., *Poly(methyl methacrylate) grafted imogolite nanotubes prepared through surface-initiated ARGET ATRP Inorganic*, Chem. Comm. 47(20) (May 28, 2011) 5813-5815.
Mukherjee, et al., *Phenomenology of the growth of single-walled aluminosilicate and aluminogermanate nanotubes of precise dimensions*, Chem. Mater. 17(20) (Oct. 4, 2005) 4900-4909.
Zang, et al., *Self-diffusion of water and simple alcohols in single-walled aluminosilicate nanotubes*, ACS Nano 3(6) (2009) 1548-1556.
PCT Nov. 20, 2012 International Search Report and Written Opinion mailed in International Patent Application PCT/US2012/054404.
Huang, et al., *Multilayer poly(vinyl alcohol)-zeolite 4A composite membranes for ethanol deyhdration by means of pervaporation*, Separation & Purification Technology 51 (2006) 126-136.
Johnson, et al., *Tubular silicate-layered silicate intercalation compounds: A new family of pillared clays*, J. Am. Chem. Soc. 110(25) (1988) 8545-8547.
Apr. 30, 2013 Office Action mailed in U.S. Appl. No. 13/049,375, filed Mar. 16, 2011.
Jul. 9, 2013 Amendment and Response to Office Action mailed on Apr. 30, 2013 in U.S. Appl. No. 13/049,375, filed Mar. 16, 2011.
Aug. 1, 2013 Notice of Allowance/Allowability mailed in U.S. Appl. No. 13/049,375, filed Mar. 16, 2011.
JP Mar. 3, 2014 Office Action mailed in international patent application JP 2013-500178 (with English translation).
KR Dec. 17, 2013 Office Action mailed in international patent application KR 10-2012-7022700 (with English translation).
KR Apr. 28, 2014 Decision to Reject a Patent mailed in international patent application KR 10-2012-7022700 (with English translation).
Mukherjee, *Synthesis, characterization, and growth mechanism of single-walled metal oxide nanotubes* (a Ph.D. dissertation, Georgia Institute of Technology 2007).
Lvov, et al., *Halloysite clay nanotubes for controlled release of protective agents*, ACS Nano 2(5) (May 2008) 815-820.
Jan. 17, 2014 Office Action mailed in U.S. Appl. No. 13/608,768, filed Sep. 10, 2012.
Apr. 17, 2014 Amendment and Response to Office Action mailed on Jan. 17, 2014 in U.S. Appl. No. 13/608,768, filed Sep. 10, 2012.
Jun. 23, 2014 Office Action mailed in U.S. Appl. No. 13/608,768, filed Sep. 10, 2012.
Sep. 19, 2014 Amendment and Response to Office Action mailed on Jun. 23, 2014 in U.S. Appl. No. 13/608,768, filed Sep. 10, 2012.
Nov. 14, 2014 Final Office Action mailed in U.S. Appl. No. 13/608,768, filed Sep. 10, 2012.
Feb. 10, 2015 Amendment and Response to Final Office Action Mailed on Nov. 14, 2014; and Request for Continued Examination filed in U.S. Appl. No. 13/608,768, filed Sep. 10, 2012.
Apr. 16, 2015 Office Action mailed in U.S. Appl. No. 13/608,768, filed Sep. 10, 2012.
Aug. 10, 2015 Amendment and Response to Office Action Mailed on Apr. 16, 2015; and Petition for One-Month Extension of Time with Exhibit A—Applicant-Initiated Interview Summary filed in U.S. Appl. No. 13/608,768, filed Sep. 10, 2012.
Aug. 31, 2015 Notice of Allowance / Allowability mailed in U.S. Appl. No. 13/608,768, filed Sep. 10, 2012.
JP Dec. 2, 2014 Final Notification of Reason(s) for Refusal mailed in Japan Patent Application 2013-500178 (with English translation).

* cited by examiner

FUNCTIONALIZED SINGLE-WALLED NANOTUBES AND METHODS THEREOF

CROSS-REFERENCE TO RELATED APPLICATIONS

The present application claims priority to U.S. Provisional Patent Application Ser. No. 61/882,910, filed on Sep. 26, 2013 for "Functionalized Single-Walled Nanotubes and Methods Thereof."

TECHNICAL FIELD

This invention relates generally to single-walled nanotube (SWNT) compositions with inclusion of organic functional units (e.g., primary amines) along the inner wall of the SWNT, and a direct synthesis of making same.

BACKGROUND OF THE INVENTION

Internal functionalization of a single-walled nanotube (SWNT) is an attractive, yet difficult challenge in nanotube materials chemistry. A still unsolved problem is how to immobilize functional moieties on its inner surface through attachment of the functional moieties to the interior surface of the inner pore wall. Doing so, particularly via a covalent bonding, would allow a number of new ways to control the properties of the SWNT and enable use of SWNTs in many applications, including those requiring molecular recognition that exploits the 1-D porosity of SWNTs (e.g., catalysis, adsorption, membranes, sensors).

The most well-known SWNT is the single-walled carbon nanotube (CNT), first prepared in 1991. The formation of covalent bonds at the CNT surface requires a transformation of carbon hybridization from $sp^2$ to $sp^3$. While this can be accomplished on the outer surface, the process requires very harsh reaction conditions. To date there has been no demonstration of interior functionalization of CNTs by the formation of covalent bonds on its interior surface or within its pore. Because the interior surface of a CNT is concave, it provides an extremely high thermodynamic obstacle for transformation. Thus, the interior surfaces of CNTs have been considered essentially unreactive. Some recent work indicates that the interior surface of CNTs may become reactive but, again, the reactivity was only made possible under very specific and very extreme conditions, a finding that further corroborates the essentially unreactive nature of the inner walls of CNTs.

Synthetic metal oxide nanotubes can potentially overcome some of the limitations observed with CNTs. An example of these nanotubes is a synthetic aluminosilicate SWNT. While some minor modifications to synthetic aluminosilicate nanotubes have been performed, the modifications were generally achieved only after synthesis via grafting, requiring a multi-step process post-synthesis and did not provide uniform distribution of the functional group along the length of the nanotube. In fact, the functionalization observed post-synthesis was only possible at the nanotube mouth or opening of the pore and the incorporation of the functional group was in line with the nanotube wall. In aluminosilicate nanotubes having inner pore diameters of 2 nm or greater, some limited functionalization was also performed; however, functionalization imparted only hydrophobicity to the inner surface of the inner pore wall and modification was highly limited to a hydrophobic methyl group, which could not be replicated with other charged functional moieties. Thus, efforts to provide functionalized SWNTs and to improve the methods for functionalization of SWNTs remain desirable.

SUMMARY OF THE INVENTION

Described herein is a composition comprising SWNTs in which the SWNTs have not only hydroxyl (—OH) groups but also organic functional units incorporated into the wall surface of the inner pore of the SWNT. Both the —OH groups and the organic functional units are covalently bonded to the inner pore wall surface of the SWNT. The organic functional units may be interspersed along the surface of the inner pore wall of the SWNT. The organic functional units may include charged functional moieties that impart a charge to the inner pore wall surface of the SWNT. The organic functional units are incorporated during synthesis by a substitution of one or more nanotube precursors with compatible organic compounds that contain the organic functional units. With substitution, the organic functional units when arranged along the surface of the inner pore wall have a portion of the organic functional units that face into and provide potential reactive sites in the inner pore space of the SWNT. The organic functional units when so arranged include a portion which extends into the inner pore space of the SWNT. In some embodiments, the organic functional units are not in line with the wall of the SWNT.

SWNTs that may be formed as functionalized SWNTs include but are not limited to metal oxide SWNTs, such as but not limited to aluminosilicate SWNTs, aluminogermanate SWNTs, nickel phyllosilicate SWNTs, and the like.

In one or more embodiments, the SWNTs are prepared from a condensable precursor containing a Group IVA element, a condensable organic compound (an organic functional unit precursor), and an oxidizing agent (metal oxide or metalloid oxide). The organic compound will have at least part of its structure compatible with or structurally similar to the condensable precursor. Both the condensable precursor and the organic compound will contain the same Group IVA element, depicted generally as X—$R_n$ or X—$(OR)_n$, in which X is the Group IVA element selected from silicon, germanium, tin and lead and n=1, 2, 3 or 4.

The organic compound has a general structure R'—X—$R_{n-1}$ or R'—X—$(OR)_{n-1}$ and further contains at least one organic functional unit R' and not more than four of the functional unit R', which is selected from hydrogen, alkyl, aryl, amino, epoxy, sulfido, vinyl, methacrylic, mercapto, isocyanate or other organofunctional group.

Synthesis of the SWNT provides a substitution of some of the Group IVA elements from the condensable precursor for the same Group IVA elements from the organic compound, each organic compound further containing one or more organic functional units. The functionalized SWNTs when formed will have the organic functional unit covalently bound to the Group WA element, such that the organic functional unit is positioned on the wall surface of the inner pore of the SWNT and extending therefrom into the inner pore space of the SWNT.

Through a type of co-condensation reaction performed under a mild aqueous and acidic condition, processes described herein provide a method of essentially substituting a portion of the condensable precursors with compatible organic compounds containing the organic functional unit, the substitutions providing functional organic units on the inner wall surface of the SWNT. The Group IVA elements make up the backbone of the wall of the SWNT. Due to the covalent bonding of the organic functional units to the Group IVA elements, the organic functional units are not in line with the wall of the SWNT. This is contrasted with in-line incorporation found with alternative methods of functionalizing SWNTs, which provides a structurally different tube wall and pore space with less lateral expansion. The organic functional units described herein also provide sites for further binding in the inner pore space of the SWNTs. These binding sites are dispersed throughout the length of the inner wall surface of the SWNTs because the organic functional units are dispersed along the length of the inner pore of the SWNT. Thus, binding sites are not limited to the mouth or opening or ends of the SWNTs. Similarly, the organic functional units are not limited to nor are they localized or constrained at the mouth, opening or ends of the SWNTs. In some embodiments, due to the structure of the organic functional units, the organic functional units when covalently bonded as described herein do not impart hydrophobicity to the inner wall surface of the SWNT. This is unlike one or more alternative methods.

In some embodiments, at least about 15% of the inner wall surface of the SWNTs are functionalized (e.g., containing the organic functional units) after synthesis as described herein. In some embodiments, the organic functional units are incorporated in an amount greater than 15% of the inner wall surface of the SWNT.

The method of making functionalized SWNT compositions described herein includes combining in an aqueous reaction mixture a condensable precursor containing at least one Group IVA element, an organic compound that is structurally compatible with the condensable precursor and containing at least one organic functional unit bonded thereto, and an oxidizing agent containing a metal. Both the condensable precursor and the organic compound will contain the same Group IVA element; the organic compound comprises an organic functional unit bound to its Group IVA element. The condensable precursor has a general structure of X—$R_n$, the organic compound has a general structure of R'—X—$R_{n-1}$, and when the condensable precursor has a general structure of X—$(OR)_n$, the organic compound has a general structure of R'—X—$(OR)_{n-1}$, in which X is a Group WA element selected from one of silicon, germanium, tin and lead. R' is at least one organic functional unit selected from one of hydrogen, alkyl, aryl, amino, epoxy, sulfido, vinyl, methacrylic, mercapto, isocyanate or other organofunctional group and combinations thereof. OR may be selected from any of a methoxy, ethoxy, propoxy or acetoxy group and combinations thereof. The aqueous reaction mixture is allowed to undergo a reaction. The condensable precursor and the organic compound may be in a ratio of (1−x) to (x).

Under acidic conditions, a type of co-condensation reaction occurs in which one or more organic functional units covalently bound to a Group WA element from the organic compound is incorporated into the wall of the SWNT, such that the one or more organic functional units face the interior or inner pore of the SWNT, thereby forming a functionalized SWNT composition. Thus, unlike previous methods in which functionalization took place only after synthesis of the SWNT, the processes described herein are a single-step process. The processes described herein do not require post-synthesis steps or grafting. The processes described herein are template free and, therefore, do not require a template for the co-condensation reaction. The combining in an aqueous reaction mixture may comprise mixing the aqueous reaction mixture initially under nitrogen followed by addition of a strong acid and stirring vigorously at an ambient temperature. The method may further comprise a step of forming a gel after undergoing the reaction. The method may further comprise a step of treating a gel that is formed after undergoing the reaction in order to obtain a powder. The reaction may also include condensing the aqueous reaction mixture at a temperature less than 100° C. The reaction mixture may further include an acid. The reaction mixture is typically at a pH of about 4.5 or less. The ratio of the condensable precursor to the organic compound to the acid may be about (1−x):(x):1. The ratio of the condensable precursor to the organic compound to the metal to the acid may be about (1−x):(x):2:1.

Also described herein are functionalized single-walled metal-oxide nanotubes prepared by the described methods. Said nanotubes will in one or more embodiments comprise a metal-oxide nanotube having a single wall and opposing ends; and a quantity of organic functional units incorporated on the inner surface of the single wall, wherein the organic functional units are covalently bound to the inner surface of the single wall, wherein the organic functional units are substituted for hydroxyl units on the inner surface of the single-wall, wherein the organic functional units bind to a component of the single wall, the component consisting of one of a Group IVA element selected from one of silicon, germanium, tin and lead, and wherein the organic functional units are incorporated at various locations along a length of the inner surface of the single wall. The metal-oxide nanotube may be an aluminosilicate nanotube. The organic functional units may contain amino groups. The quantity of organic functional units may be at least about 15%. The organic functional units may be dispersed uniformly at the various locations along the length of the inner surface of the single wall. At least some of the organic functional units do not impart hydrophobicity to the inner surface of the single-wall. In some embodiments, the organic functional units are not localized at one or more of the opposing ends of the single wall. The organic functional units may include organic functional units that are not sterically capable of being incorporated along a length of the inner surface of the single-wall were the organic functional units to be incorporated after synthesis of the metal-oxide nanotube. The organic functional units are incorporated on the inner surface of the single wall during synthesis of metal-oxide nanotubes.

These and other objects, features, and advantages will become apparent as reference is made to the following detailed description, preferred embodiments, and examples, given for the purpose of disclosure, and taken in conjunction with the accompanying drawings and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature and objects of the present invention, reference should be made to the following detailed disclosure, taken in conjunction with the accompanying drawings, in which like parts are given like reference numerals, and wherein:

FIGS. 2A-2C illustrate representative images of SWNTs prepared in accordance with a method associated with FIG. 1A, in which FIG. 2A is a conventional transmission electronic microscopy (TEM) image with the scale bar representing 20 nm, FIG. 2B is a cryo-electron microscopy (cryo-EM) image with the scale bar representing 10 nm, and FIG. 2C is an electron diffraction pattern (ED) with reflections numbered 1-5 assigned to (006), (004), (063), (071), and (002), respectively;

FIGS. 2D-2F illustrate representative images of SWNTs prepared in accordance with a method associated with FIG. 1B as described herein, in which FIG. 2D is a TEM image with the scale bar representing 20 nm, FIG. 2E is a cryo-EM image with the scale bar representing 20 nm, and FIG. 2F is an ED pattern with reflections numbered 1, 3, and 5 assigned to (006), (063), and (002), respectively;

DETAILED DESCRIPTION OF PREFERRED EMBODIMENTS OF THE INVENTION

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

Described herein are synthetic SWNT compositions functionalized in a single step process. The functionalized SWNTs will include at least one element from the Group IVA elements (Group 14 of the periodic chart) that include silicon, germanium, tin and lead. Elements neighboring the Group IVA elements, including phosphorus and arsenic, are also precursor candidates to form synthetic nanotubes described herein.

Figure 1A:
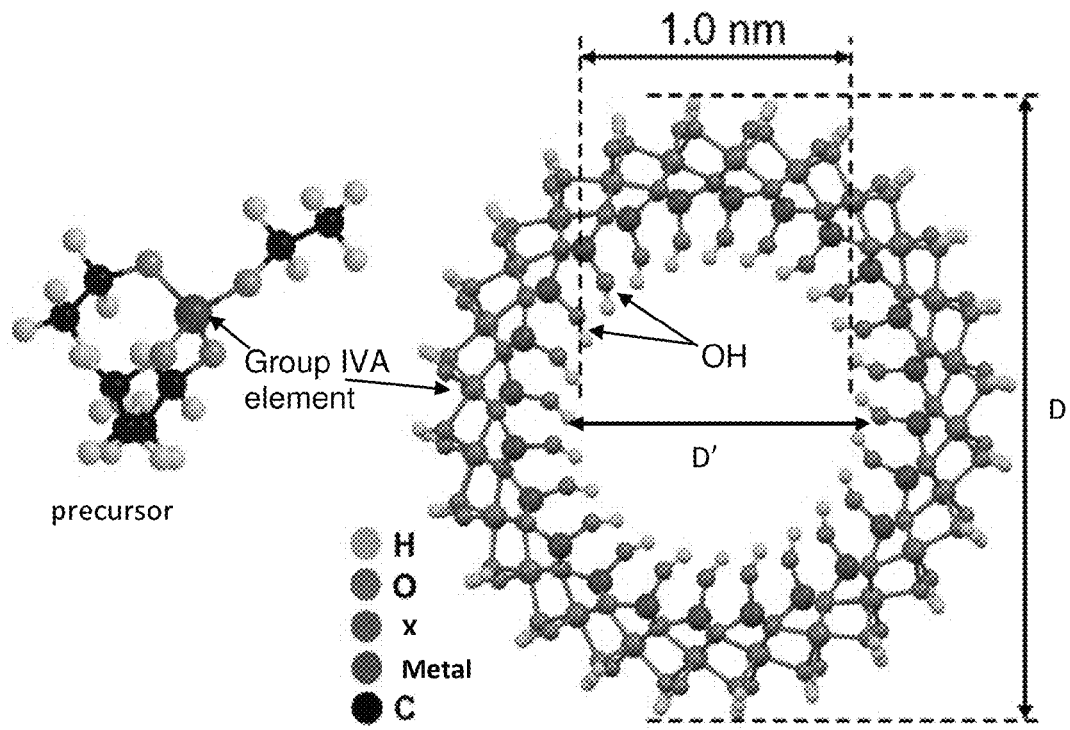
FIG. 1A illustrates a schematic of a process involving synthesis of bare or nonfunctionalized SWNTs using a condensable precursor containing a Group IVA element as a starting reagent.

The functionalized SWNTs described herein are contrasted with non-functionalized SWNTs, as illustrated in the cross section in FIG. 1A (right). Typically, non-functionalized SWNTs are prepared from a starting reagent or precursor containing a Group IVA element as depicted in FIG. 1A (left). The Group IVA element (see X in FIG. 1A) forms a backbone of the precursor and also forms the wall of the SWNTs. A non-functionalized or bare SWNT is crystalline, has a cross-sectional diameter D and an inner pore D' that generally spans the length of the nanotube, as illustrated in FIG. 1A (right). The inner pore of nonfunctionalized SWNTs will have a surface lined solely with —OH groups bonded to the Group IVA elements. Using silicone (Si) as an example of a Group IVA element, the surface of an inner pore of a SWNT in which the wall is composed of Si, will have its inner pore lined with Si—OH (silanol). Typically, to create a functionalized SWNT, a fully formed and synthesized SWNT must undergo additional reaction steps (post-synthesis) in the presence of an acid chloride, alcohol, or silane to facilitate modification and substitution of the —OH groups.

Direct Synthesis of Single-Walled Nanotube Compositions

Figure 1B:
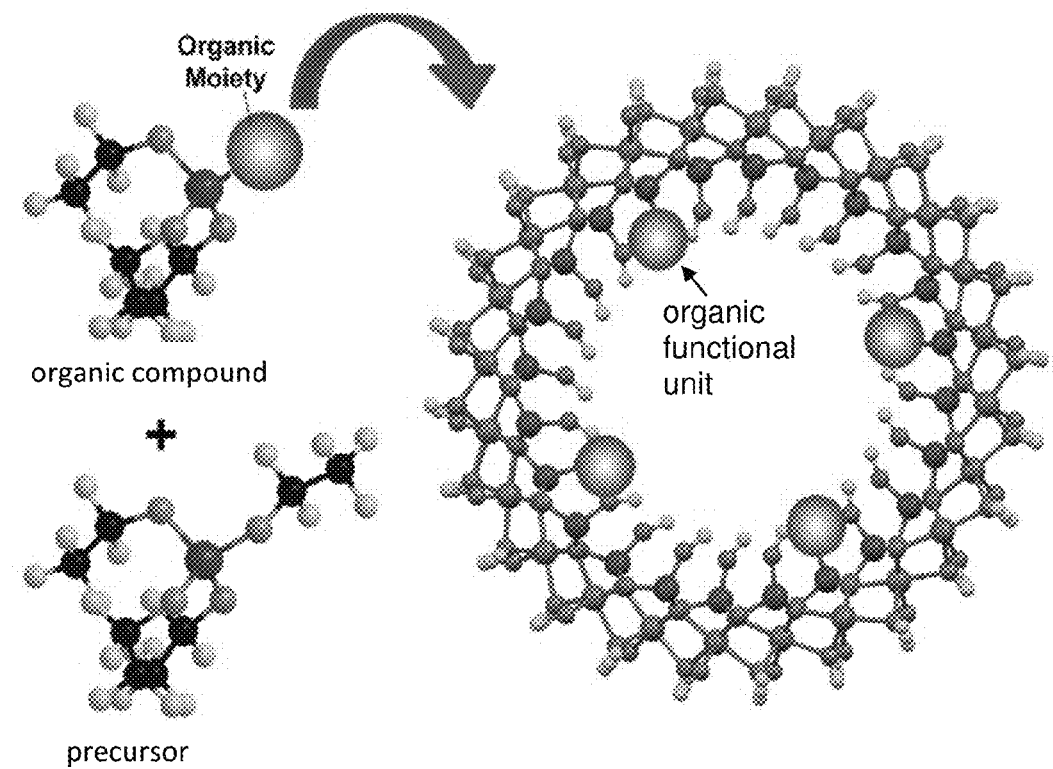
FIG. 1B illustrates a schematic of a process of forming functionalized SWNTs as described herein using a condensable precursor containing a Group IVA element and an organic compound containing an organic functional unit as starting reagents, such that upon synthesis, there is substitution of at least a portion of the condensable precursors for the organic compounds containing the organic functional units.
Figure 2A:
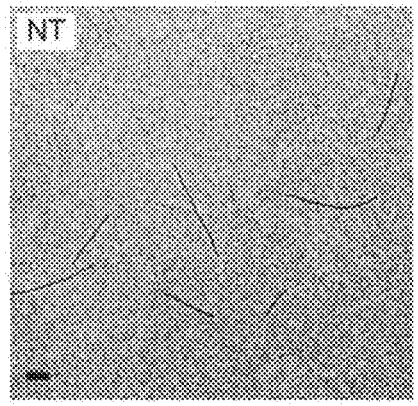
Figure 2D:
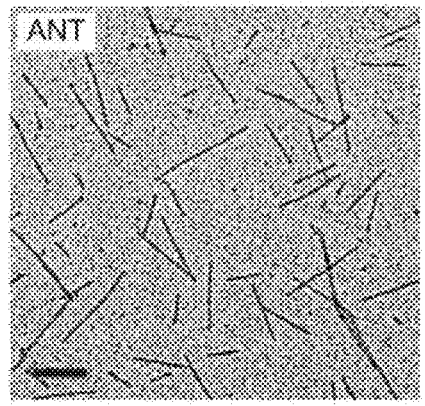
Figure 2B:
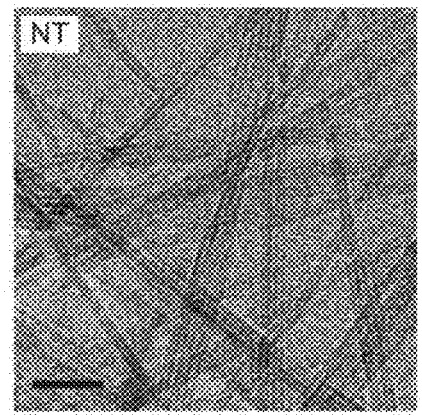
Figure 2E:
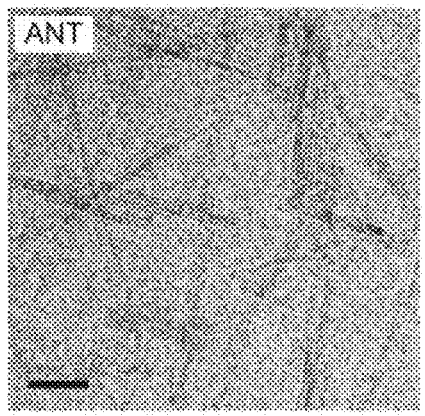
Figure 2C:
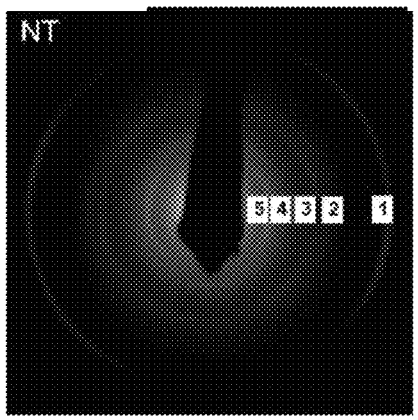
Figure 2F:
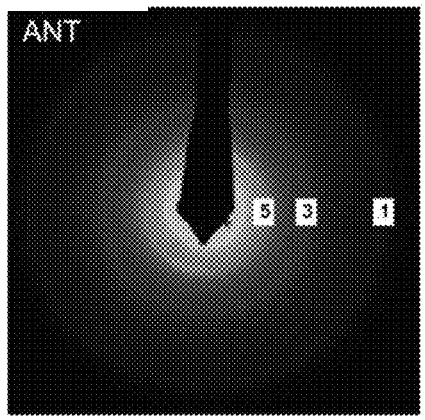

The formation of the SWNT compositions described herein is based upon an aqueous-phase synthesis under mild conditions. Synthesis includes a co-condensation reaction at a temperature that is generally at or less than about 100° C. Temperatures greater than about 100° C. are also suitable. The reaction includes a condensable precursor containing a Group IVA element and an organic compound containing at least one organic functional moiety (organic functional unit). This is illustrated generally in FIG. 1B (left). While one organic moiety is illustrated in FIG. 1B, up to three organic moieties may be bound to the Group IVA element of the organic compound, which may or may not be the same type of organic moiety.

The co-condensation in an aqueous solution under mild conditions as described herein results in the formation of functionalized SWNTs that have an inner pore surface to which a plurality of —OH groups are now substituted by the organic functional units, which remain bound to the organic compound. Because the organic compound also contains the same Group IVA element that is part of the condensable precursor and because the organic compound is selected to be structurally compatible with the condensable precursor, the organic compound is, in fact, substituted into the formed SWNT (replacing the condensable precursor). As a result, the organic functional units are not in line with the inner wall of the formed SWNT (as is often found with modification made post-synthesis), but form (because of the covalent bonding) part of the surface of the inner pore (e.g., extending away from the wall). The organic functional units remain covalently bonded to its Group WA element and are substituted for the precursor. Depending on its size and structure, some organic functional units will extend into the inner pore space of the SWNTs.

For processes described herein, when the condensable precursor has a general structure of X—$R_n$, the organic compound will have a general structure of R'—X—$R_{n-1}$, in which X is a Group IVA element that is the same in both the condensable precursor and the organic compound and is selected from one of silicon, germanium, tin and lead, and in which R' is the organic functional unit selected from one of hydrogen, alkyl, aryl, amino, epoxy, sulfido, vinyl, methacrylic, mercapto, isocyanate or other organofunctional group and combinations thereof.

Similarly, when the condensable precursor has a general structure of X—$(OR)_n$, the organic compound has a general structure of R'—X—$(OR)_{n-1}$, in which X and R' are the same is defined above and OR is any of a methoxy, ethoxy, propoxy or acetoxy group and combinations thereof.

The synthesis of nanotubes as described herein, with the direct inclusion of functional units, is not believed to have been previously disclosed. Synthetic functionalized nanotubes that may be prepared by the methods described herein include but are not limited to aluminosilicate nanotubes, aluminogermanate nanotubes, nickel phyllosilicate nanotubes, synthetic imogolite-like nanotubes, and synthetic halloysite-like nanotubes, as examples.

The synthesis method described herein requires essentially only one reaction with the described reagents (condensable precursor containing a Group IV element, organic compound containing the organic functional unit, and oxidizing agent containing a metal) to prepare functionalized SWNTs. This is contrasted with alternative modification processes that occur post-synthesis. Moreover, the as-synthesized functionalizations described herein provide structurally different SWNTs than SWNTs prepared by a modification after synthesis. The differences include differing pore diameters, different gas separation characteristics as well as differences in where the organic functional units are positioned with reference to the wall (and the Group IVA element) of the SWNTs.

Example of Aluminosilicate Nanotubes Functionalized with Aminomethyl Groups

In a representative example, functionalized metal oxide nanotubes were prepared using a condensable precursor, tetraethyl orthosilicate (TEOS), and a compatible organic compound, aminomethyltriethoxysilane (AMTES), which contains alkyl amine functional groups. The AMTES was synthesized by treating a commercially available chloromethyltriethoxysilane with gaseous ammonia using a Parr reactor and reacting anhydrously at 900-1000 psi and 100° C. for five hours (see e.g., Brunelli, N. A., et al., *J. Am. Chem. Soc.,* 134 (2012) 13950). The precursor and compatible organic compound were mixed with an oxidizing agent, aluminum-tri-sec-butoxide, in a glove box filled with nitrogen. The reaction mixture included molar amounts of TEOS:AMTES:Al:$HClO_4$ in a ratio of (1−x):x:2:1. The precursor, compatible organic compound and oxidizing agent were added to a Teflon jar (1000 mL capacity) containing 500 mL of a strong acid (38 mM perchloric acid). The pH was 4.5 or less. When x=0.2 or 0.5 or 1, functionalized nanotubes (ANTs) were synthesized. Data for synthesis products with x=0.5 and 1 are not shown.

Nonfunctionalized or bare synthetic single walled nanotubes (NTs) were formed using similar reaction conditions, in which x=0 for the above-described ratio of TEOS:AMTES:Al:$HClO_4$. The bare NTs, as aluminosilicate nanotubes, had an octahedral aluminum(III) hydroxide outer wall and doubly-coordinated hydroxyl groups on the outer wall with a tetrahedral silanol inner wall that included pendant hydroxyls thereon. The hydroxyls extended into and form the surface of the inner pore wall of the bare nanotubes.

For preparing both the exemplary bare NTs (not containing the compatible organic compound) and the exemplary functionalized ANTs (containing the compatible organic compound with the alkyl amine functional group), the aqueous reaction mixture was vigorously stirred at an ambient (room) temperature for 24 hours. The solution was then diluted with distilled water by a factor of 3.8 with respect to volume, and then stirred at 95° C. for 96 hours. Once the temperature was about 95° C., the solution turned from cloudy to clear in about one hour.

For gelation of suspended nanotubes (which is optional), the solution was cooled to room temperature and the pH adjusted, such as with a 30 wt. % ammonia solution added dropwise. This forces the nanotubes to form bundles in a gel. Once formed as a gel, the gel can be isolated (e.g., centrifuge at 7000 rpm for 10 minutes and discard the supernatant). Nanotubes could be redispersed with a few drops of an acid (e.g., 10 N hydrochloric acid).

Purification of the nanotubes may include dialysis (e.g., against 10 wt. % ammonium hydroxide solution for 24 hours followed by distilled water for 3 days, using a membrane having a 15 kDa molecular weight cutoff).

To obtain powder samples, a purified gel may be dried and dispersed (e.g., heated to 60° C. and then ground lightly to disperse any agglomerated nanotubes).

In exemplary methods, which included gelation and purification, approximately 1 g of a powder sample was obtained from a 1 liter synthesis batch volume.

Evaluation of Functionalized Single-Walled Nanotubes

Samples of the exemplary nonfunctionalized NTs and the exemplary functionalized ANTs were evaluated by TEM (see FIG. 2), XRD (see FIG. 6), NMR (see FIGS. 3-5, TABLES 2 & 3), gas absorption (see FIG. 7, TABLE 4), nitrogen physical adsorption ($N_2$ physisorption; see TABLE 3) and elemental analysis (see TABLES 1 & 3).

Figure 8:
FIG. 8 illustrates an ED pattern with reflections numbered 1-5 assigned to (006), (004), (063), (071), and (002), respectively, for SWNTs modified by methyltrimethoxysilane using an alternative method than what is described herein.

The morphology was evaluated by conventional and cryo-TEM. TEM images were collected using a JEOL JEM-2200FS 200 kV field emission transmission electron microscope with an in-column Omega energy filter (operated at 200 kV) (see e.g., Yucelen, G. I., et al., Nano Lett., 12 (2012) 827). Cryo-TEM images were recorded using a JEOL JEM-1210 microscope operated at 100 kV (see e.g., Kang, D.-Y., et al., ACS Nano, 4 (2010) 4897). Representative low-resolution images of NTs (see FIG. 2A) and ANTs (see FIG. 2D) are illustrated, in which ANTs had, on average, a smaller length than NTs, such that the average length of NTs was 160 nm and for ANTs was 50 nm. Higher-resolution cryo-TEM images of NTs (see FIG. 2B) and ANTs (see FIG. 2E) confirmed the general nanotubular structures. ED was used to investigate crystallinity along the axis of NTs (see FIG. 2C) and ANTs (see FIG. 2F), which showed an ordered nanotube wall structure for both functionalized and non-functionalized nanotubes. The NT reflections (006), (071), and (002) became less sharp while ANT reflections (004) and (063) were weak or absent in its ED pattern (see e.g., Kang, D. Y., et al., Phys. Chem. C, 115 (2011) 7676). Interestingly, the ED patterns were contrasted with those taken from nanotubes that were synthesized in a manner similar to the NTs and thereafter functionalized (post-synthesis) with methyltrimethoxysilane (see FIG. 8). Together, these figures shows that functional units on the nanotubes functionalized post-synthesis were localized at the pore mouth and the ED pattern was nearly identical to the pattern from NTs. Thus, functionalization on the nanotubes described herein appears to be non-uniform and non-localized with a distribution that is random, along the length of the wall surface of the inner pore.

Figure 9:
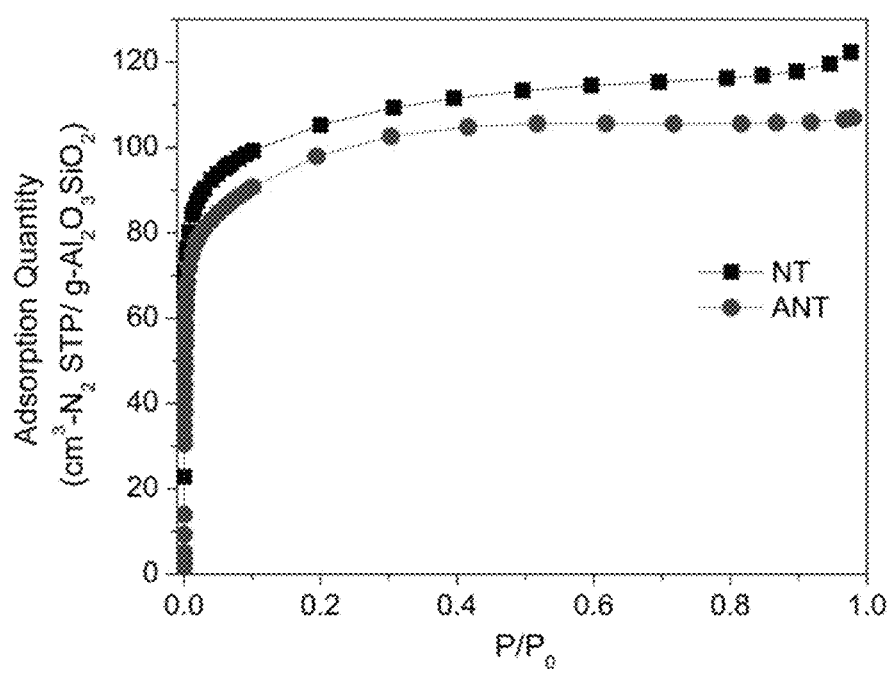
FIG. 9 illustrates a raw $N_2$ physisorption isotherm for SWNTs prepared in accordance with a method associated with FIG. 1A (squares) or in accordance with a method associated with FIG. 1B (circles)

A combination of $N_2$ physisorption (to estimate the expected pore volume reduction due to functionalized/functional unit substitution), $^{13}C$ solid-state NMR, FT-Raman spectroscopy, and elemental analysis was used to evaluate the interior surface properties of the functionalized nanotubes described herein. Raw $N_2$ physisorption isotherms are illustrated in FIG. 9. These measurements were carried out on a Micromeritics Tristar II at 77° K. For measurements, a sample was placed in an analysis tube and degassed under 15 mTorr at 200° C. for 12 hours before physisorption measurements. The lower pore volume of the ANTs is attributed to the larger size of the immobilized functional group after functionalization, which in the representative example was an aminomethyl group ($\equiv Si-CH_2NH_2$). This is compared to the smaller hydroxyl group ($\equiv Si-OH$) residing in the interior pore of the non-functionalized nanotubes. Given the volumes of the hydroxyl and the aminomethyl groups (16.9 and 38.1 Å$^3$, respectively, as estimated from the atomic van der Waals radii), the fractional organic substitution ratio in the ANTs was calculated by comparing the micropore volume of NT and ANT. The derived fractional organic substitution was 0.16, which is close to the AMTES:TEOS ratio (0.2) used for synthesis of the functionalized nanotubes. The atomic compositions derived from elemental analysis are summarized in TABLE 1A, in which the values represent molar elemental ratios normalized to silicon, such that Al is aluminum, Si is silicone, C is Carbon and N is nitrogen.

TABLE 1A

| NT | | | | ANT | | | |
|---|---|---|---|---|---|---|---|
| Al | Si | C | N | Al | Si | C | N |
| 1.99 | 1.00 | 0.00 | 0.00 | 2.00 | 1.00 | 0.16 | 0.11 |

Raw elemental analysis are presented in TABLE 1B.

TABLE 1B

| NT | | | | ANT | | | |
|---|---|---|---|---|---|---|---|
| Al | Si | C | N | Al | Si | C | N |
| 30.0% | 15.6% | 0% | 0% | 28.0% | 14.5% | 1.0% | 0.7% |

The elemental analysis showed a nearly identical Si:Al ratio of 0.5 in both the ANTs and NTs, which ruled out the presence of impurities caused by self-polymerization of the reagents (the condensable precursor or compatible organic compound, TEOS or AMTES, respectively) during the synthesis. The presence of nitrogen and carbon signals only in ANTs verified the presence of these organic elements and hence the organic functional units in the functionalized nanotubes. The fractional organic substitution estimated from the carbon signal (0.16) and from the nitrogen signal (0.11) was also consistent with the quantification from $N_2$ physisorption reported above (which was 0.16). The $N_2$ physisorption and elemental analysis data further verified the presence of immobilized organic functional units in the ANTs.

$^{13}C$ solid-state NMR and FT-Raman spectroscopy were used to identify the organic species. In general, magnetic angle spinning (MAS) NMR measurements for $^{13}C$, $^{27}Al$, and $^{29}Si$ were carried out on a Bruker DSX 300 using a 7 mm rotor. For $^{13}C$ cross-polarization (CP) MAS NMR, the sample was spun at 5 kHz using a single $\pi/2$ pulse with duration of 5 μsecond and a repetition time of 4 seconds. For $^{27}Al$ MAS NMR, the sample was spun at 5-6 kHz using a single pulse of $\partial/6$ (duration 0.6 μseconds) and a repetition time of 0.1 seconds. For $^{29}Si$ MAS NMR, direct polarization (DP) scans were performed with repetition times of 10 seconds at $\partial/2$ single pulse (duration 5 μseconds) and 5 kHz spinning rate. The chemical shifts of $^{13}C$, $^{27}Al$, and $^{29}Si$ were referenced to adamantane ($^{13}C$ chemical shift at 38.45 ppm), an aqueous solution of aluminum trichloride ($^{27}Al$ chemical shift at 0 ppm), and solid 3-(trimethylsilyl)-1-propanesulfonic acid sodium salt ($^{29}Si$ chemical shift at 0 ppm), respectively.

Figure 3A:
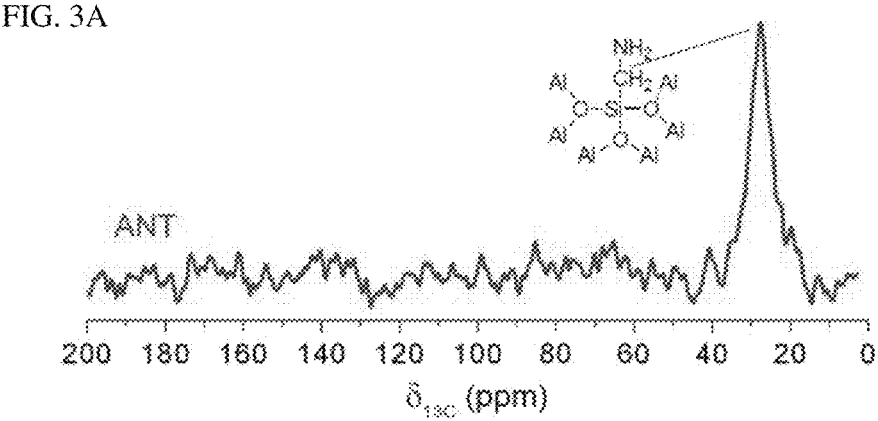
FIG. 3A illustrates a representative $^{13}C$ solid-state nuclear magnetic resonance (NMR) spectrum of SWNTs prepared in accordance with a method associated with FIG. 1B.

Referring to FIG. 3A, the single peak at 27 ppm in the $^{13}C$ NMR spectrum of ANT was assigned to the functional unit (the aminomethyl group) incorporated in the nanotubes. The absence of peaks from ethoxy groups (57 ppm for —OCH$_2$— and 17 ppm for —CH$_3$) provided by the compatible organic compound (AMTES) corroborated the success and functionalization during ANT synthesis (see e.g., Ek, S., et al., J. Phys. Chem. B, 108 (2004) 11454). It is known that when using the precursor, TEOS, for bare nanotube synthesis, the ethoxy groups are hydrolyzed and a Q$^3$(6Al)$\equiv$Si—OH coordination environment is formed (see e.g., Kang, D.-Y., et al., ACS Nano, 4 (2010) 4897; Yucelen, G. I., et al., J. Am. Chem. Soc., 133 (2011) 5397; Kang, D. Y., et al., J. Phys. Chem. C, 115 (2011) 7676). However, this coordination was exclusively found only in the NTs. In the single-walled functionalized nanotubes described herein that underwent functional unit substitution (e.g., aminomethylsilane substitution), hydrolysis of ethoxy groups and formation of an equivalent T$^3$(6Al) $\equiv$Si—CH$_2$NH$_2$ environment was observed (see e.g., Kang, D.-Y., et al., ACS Nano, 4 (2010) 4897; Kang, D. Y., et al., J. Phys. Chem. C, 115 (2011) 7676).

Figure 3B:
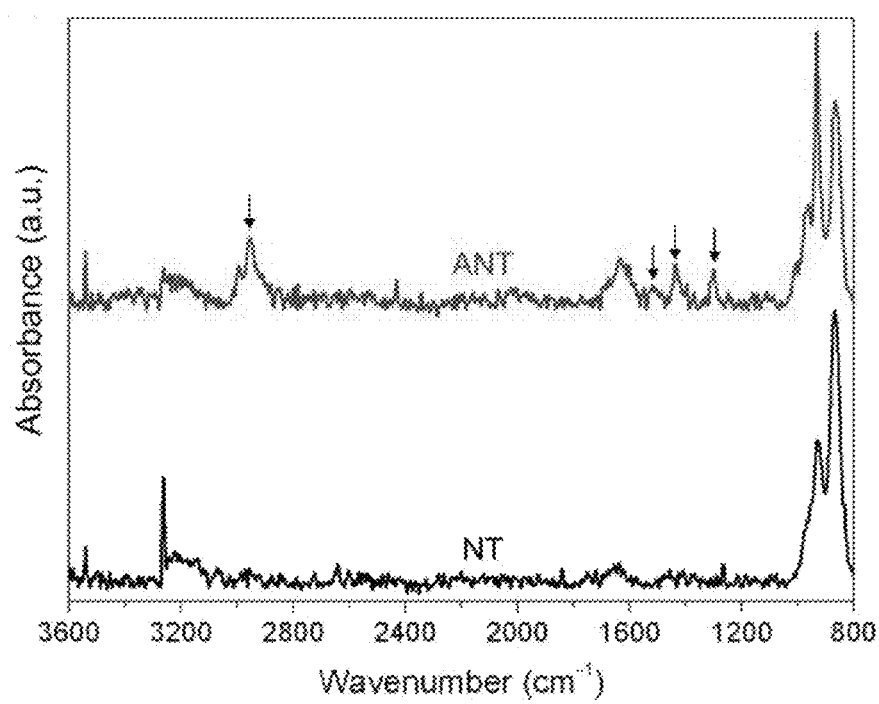
FIG. 3B illustrates a representative Fourier transform (FT)-Raman spectra of SWNTs, in which the top spectra is in accordance with a method associated with FIG. 1B and the bottom spectra is for SWNTs prepared in accordance with a method associated with FIG. 1A.

FT-Raman spectra for both NTs and ANTs are illustrated in FIG. 3B, obtained on a Bruker Vertex 80v spectrometer with dual FT-IR and FT-Raman benches and a $CaF_2$ beamsplitter. The additional peaks (see arrows at 1298, 1450, 1506, and 2950 cm$^{-1}$) found in the ANTs (upper spectra), absent in the NTs (lower spectra), were assigned to C—N stretching, C—H deformation, C—N deformation, and C—H stretching vibrations respectively (see e.g., Socrates, G., INFRARED AND RAMAN CHARACTERISTIC GROUP FREQUENCIES: TABLES AND CHARTS (Wiley, Chichester ed., 3d ed., 2001)). These vibrational modes further confirm the presence of the functional unit (aminomethyl groups) in the ANTs.

Figure 4A:
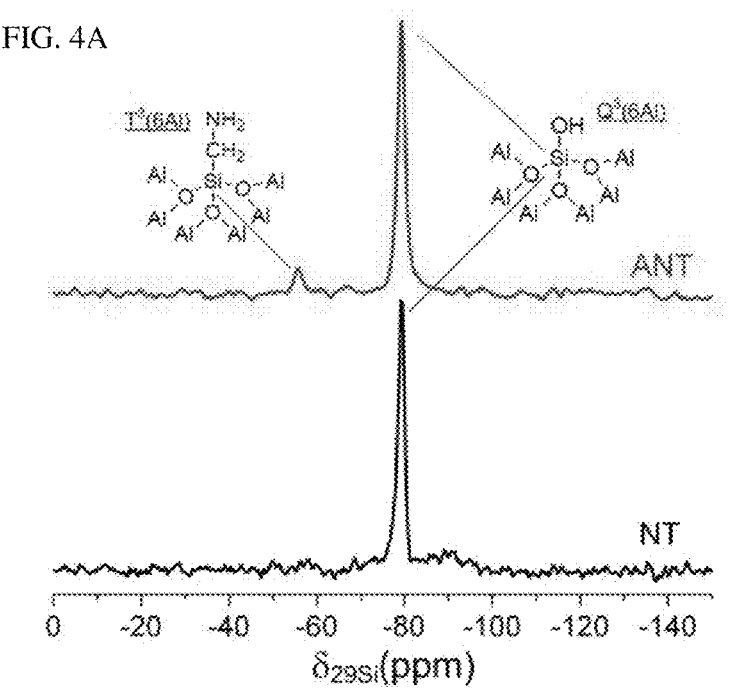
FIG. 4A illustrates a representative $^{29}Si$ direct polarization (DP) scans of SWNTs prepared, in which the top scan is in accordance with a method associated with FIG. 1B, and the bottom scan is in accordance with a method associated with FIG. 1A.
Figure 10:
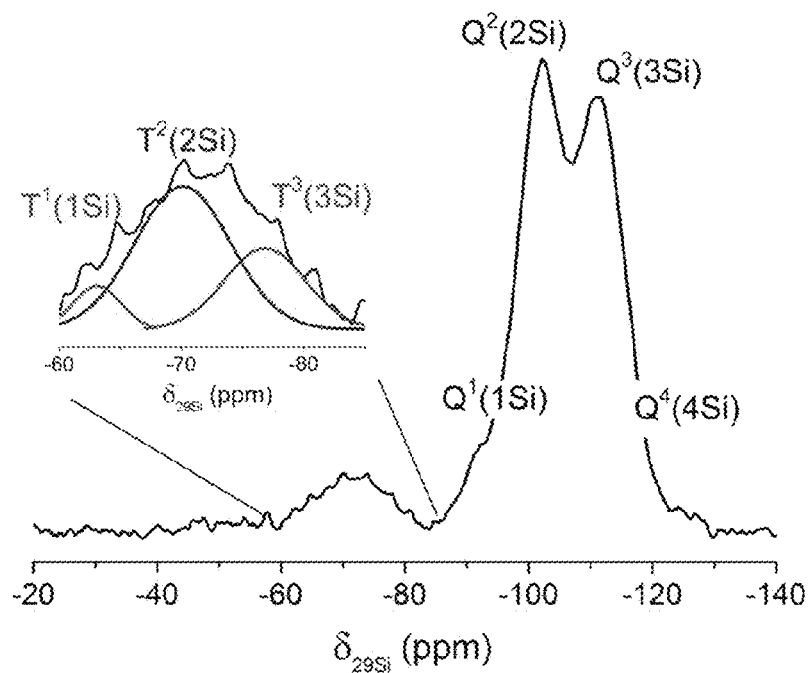
FIG. 10 illustrates a raw $^{29}Si$ NMR spectrum of a compatible organic compound (used for preparing SWNTs in accordance with the method of FIG. 1B) immobilized on a mesoporous silica support, in which T groups, which typically cover 15-20 ppm in the $^{29}Si$ spectra, denote the silicon coordination arising from the compatible organic compound, and Q groups denote the silicon coordination in the mesoporous silica support from the precursor.

The Si coordination in the ANTs was rigorously assessed by $^{29}$Si and $^{27}$Al NMR. A representative $^{29}$Si DP NMR spectra is shown in FIG. 4A for NTs (bottom) and ANTs (top), both of which had a peak at about −79 ppm, also referred to as the $Q^3$(6Al) ≡Si—OH fingerprint, from the use of TEOS as the Si source for both the functionalized and non-functionalized nanotubes (see e.g., Kang, D.-Y., et al., *ACS Nano*, 4 (2010) 4897; Yucelen, G. I., et al., *J. Am. Chem. Soc.*, 133 (2011) 5397; Kang, D. Y., et al., *J. Phys. Chem. C*, 115 (2011) 7676). A peak at −57 ppm was observed only in ANTs and occurred from the additional Si source, which was the compatible organic compound (AMTES), which was only used for ANT synthesis. The peak at −57 ppm was either $T^3$(3Si), and due to self-polymerization of the compatible organic compound) or $T^3$(6Al) Si (as a fingerprint of the isolated functional units in the functionalized nanotubes). To differentiate between these two possibilities, a control experiment was performed by immobilization of AMTES on a mesoporous silica support (SBA-15). The immobilization resulted in a combination of $T^1$(1Si), $T^2$(2Si), and $T^3$(3Si) coordinations. A raw $^{29}$Si NMR spectrum is presented in FIG. 10. The $^{29}$Si chemical shift of the $T^3$(3Si) silicon was found at −72 ppm, which was quite different from the −57 ppm chemical shift seen in the ANTs. Thus, it was concluded that the observed peak at −57 ppm in FIG. 4A was very likely due to the isolated functional unit (≡Si—CH2NH2) in the ANTs.

Figure 11:
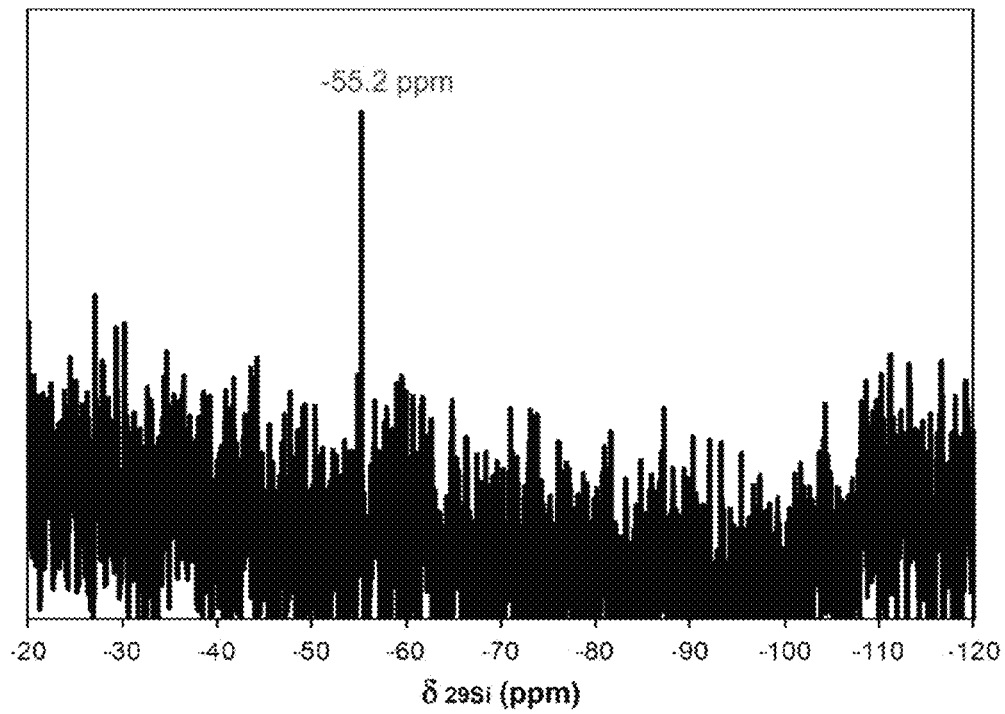
FIG. 11 illustrates a $^{29}Si$ solution-state NMR spectrum of a compatible organic compound (used for preparing SWNTs in accordance with the method of FIG. 1B) dissolved in water forming a homogeneous solution.
Figure 12:
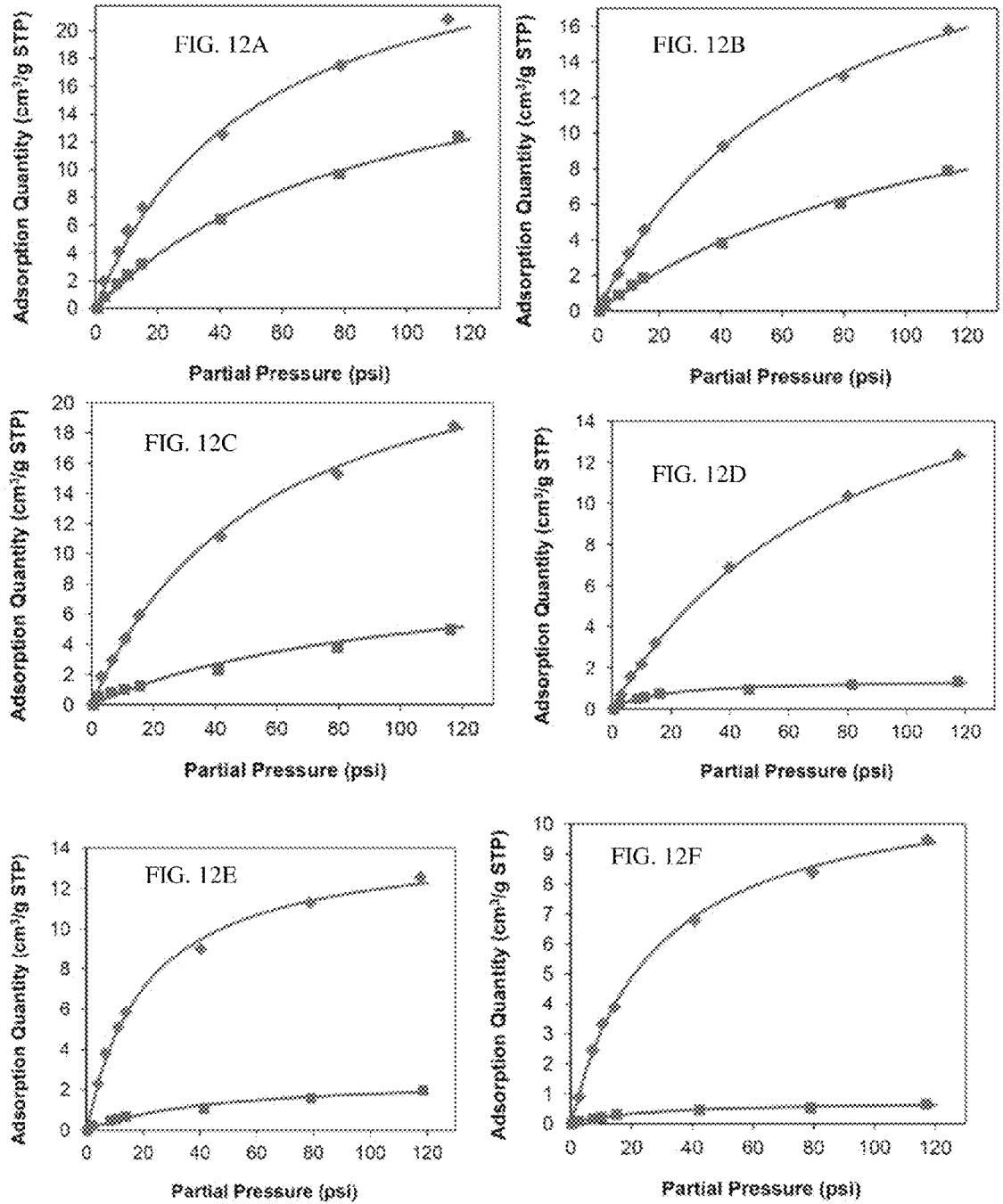
FIGS. 12A-12F illustrate adsorption isotherms of (A) $CO_2$ at 25° C., (B) $CO_2$ at 67° C., (C) $CH_4$ at 25° C., (D) $CH_4$ at 67° C., (E) $N_2$ at 25° C., and (F) $N_2$ at 67° C., in which diamonds represent SWNT prepared in accordance with a method associated with FIG. 1A and squares represent SWNT prepared in accordance with a method associated with FIG. 1B, each curve fitted with the Langmuir model.

The quantification of the fractional substitution of $T^3$(6Al) for $Q^3$(6Al) is summarized in TABLE 2. A 2 ppm chemical shift was observed for $T^0$ (−55 ppm) and $T^3$(6Al) (−57 ppm). The $T^0$ shift was obtained from the $^{29}$Si solution-state NMR spectrum of AMTES in water (see FIG. 11). The low signal-to-noise ratio in FIG. 11 is due to the low solubility of AMTES in water and low natural abundance for $^{29}$Si isotope. Provided that the repetition delay was chosen long enough, the integrated areas under the −57 ppm and −79 ppm Si peaks in the DP NMR spectrum can be used for quantifying the fractional substitution of ≡Si—CH$_2$NH$_2$ for ≡Si—OH groups. For the ANT sample, this quantity was determined to be 0.18. The $T^1$(1Si, 2Si, and 3Si) shifts were obtained from the $^{29}$Si solid-state NMR spectrum of AMTES immobilized on SBA-15 (see FIG. 10).

The fractional substitution of $T^3$(6Al) for $Q^3$(6Al) in synthetic ANTs is presented in TABLE 3.

TABLE 3

| Elemental Analysis (Nitrogen) | Elemental Analysis (Carbon) | $N_2$ Physioabsorption | $^{29}$Si Solid-State NMR | Ave. |
|---|---|---|---|---|
| 0.11 | 0.16 | 0.16 | 0.18 | 0.15 |

Figure 4B:
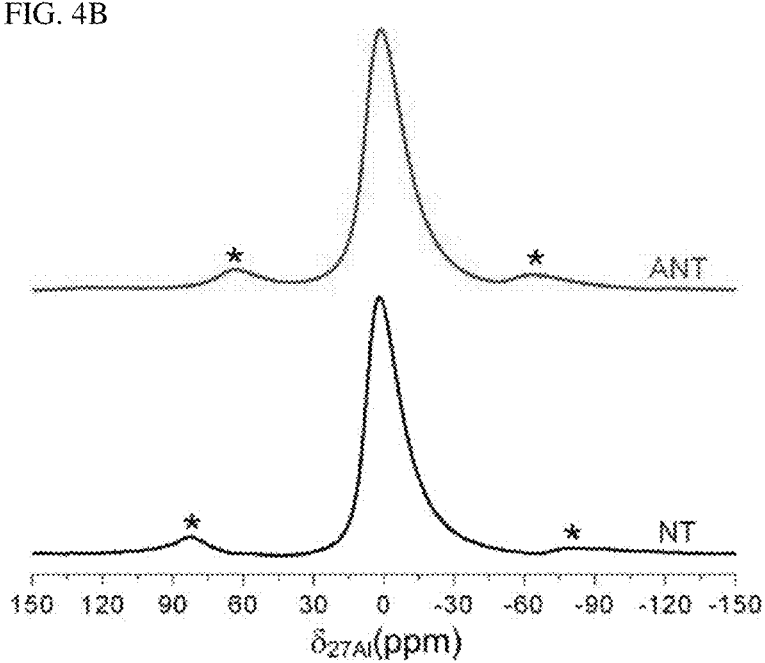
FIG. 4B illustrates a representative $^{27}Al$ solid-state NMR spectra of SWNTs, in which the top spectra is in accordance with a method associated with FIG. 1B, and the bottom spectra is in accordance with a method associated with FIG. 1A.

The $^{27}$Al spectra of NTs and ANTs were nearly identical as illustrated in FIG. 4B. The peak at −4 ppm was due to the octahedral Al coordination in both the functionalized and the non-functionalized nanotubes.

Figure 5:
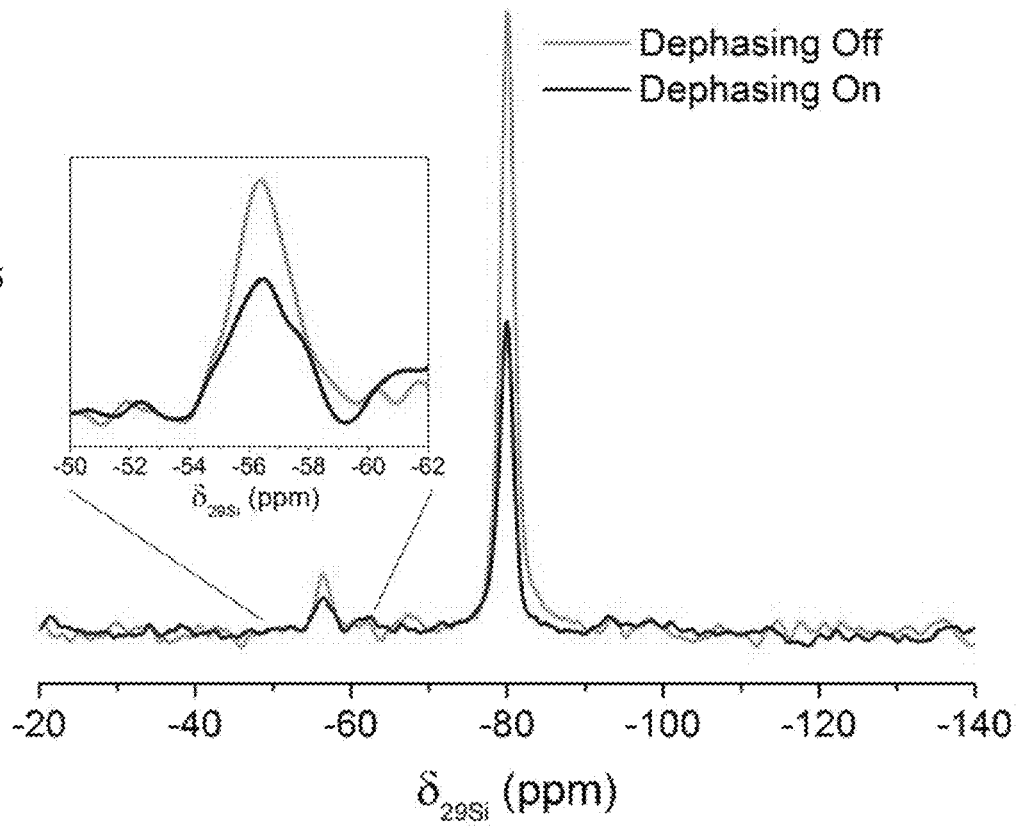
FIG. 5 illustrates a representative Transfer of Populations in Double Resonance (TRAPDOR) spectra for SWNTs prepared in accordance with a method associated with FIG. 1B.
Figure 13:
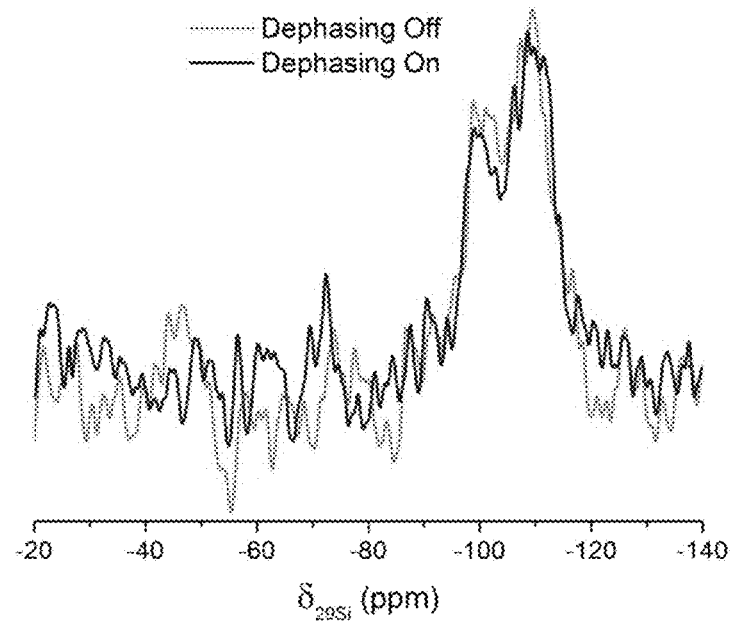
FIG. 13 illustrates $^{29}Si/^{27}Al$ TRAPDOR results for a physical mixture of a mesoporous silica support and a-alumina.

The connectivity between Si (from both TEOS and AMTES as Si sources) and Al atoms in the ANT wall was evaluated using $^{29}$Si/$^{27}$Al TRAPDOR experiments with a triple resonance probe equipped for 3.2 mm MAS rotors on a Bruker Avance III 400 (see e.g., Grey, C. P., et al., *J. Am. Chem. Soc.*, 117 (1995) 8232). The pulse sequence followed previous literature using decoupling of the $^{27}$Al-nucleus during the evolution period (see e.g., Venkatasubramanian, A. et al., *J. Phys. Chem.*, 116 (2012) 15313). The MAS spinning speed was set to 5 kHz. A dephasing time of 2 ms (10 rotor periods) was applied for the $^{27}$Al decoupling with a frequency of ca. 100 kHz. TRAPDOR directly probes the dipolar coupling between a spin=½ nucleus ($^{29}$Si) and a spin>½ nucleus ($^{27}$Al), and thereby characterizes the proximity of these two nuclei (see e.g., Grey, C. P., et al., *J. Am. Chem. Soc.*, 117 (1995) 8232); Holland, G. P., et al., *Phys. Chem. Chem. Phys.*, 7 (2005) 1739). Practically speaking, in the presence of a dephasing pulse from the $^{27}$Al channel, the $^{29}$Si peak intensity will be reduced if the Si atoms are within a few Angstroms of the Al atoms (id.). The TRAPDOR spectra for ANTs are shown in FIG. 5. A clear intensity reduction was found for both $Q^3$(6Al) and $T^3$(6Al) peaks in the presence of the $^{27}$Al dephasing pulse, confirming the close proximity between Al and Si atoms and therefore the peak assignment. In the control sample composed of a physical mixture of mesoporous silica (SBA-15) and α-alumina no intensity reduction of the Si signal was observed due to a lack of silicon-aluminum connectivity (see FIG. 13).

Figure 6A:
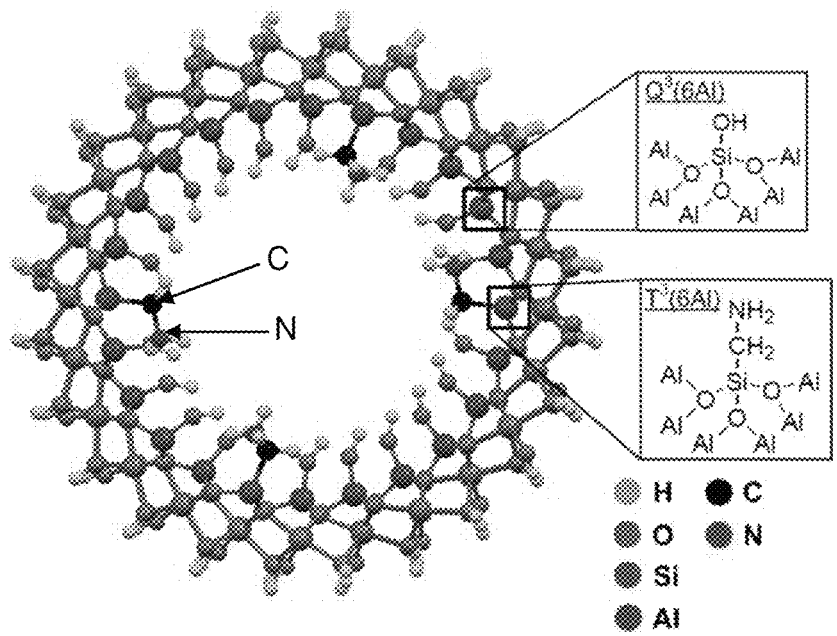
FIG. 6A illustrates a schematic of a structural model of SWNTs prepared in accordance with a method associated with FIG. 1B.

In view of the above interior surface chemistry and framework characterizations, a structural model of the exemplary functionalized nanotubes was constructed (see FIG. 6A). With the structural models of the NTs and ANTs, XRD simulations were performed (measurements in Bragg-Brentano geometry and grazing-angle XRD scans) with a diffractometer (PAnalytical X'pert Pro MPD) operating with a Cu K α source. Diffraction data were collected with a collimator and

TABLE 2

| | Si framework | | | | |
|---|---|---|---|---|---|
| | $T^0$ | $T^1$(1Si) | $T^2$(2Si) | $T^3$(3Si) | $T^3$(6Al) |
| Chemical Shift | −55 | −63 | −77 | −77 | −57 | proportional (Miniprop) He-filled detector, in the range of 3-30° 2 θ and a step size of 0.05° 2 θ. XRD pattern simulations used a software module (Reflex module of the Materials Studio 3.2 package, Accelrys) (see e.g., Kang, D.-Y., et al., *ACS Nano*, 4 (2010) 4897).

Simulated and experimental XRD patterns for NTs and ANTs are represented in

Figure 6B:
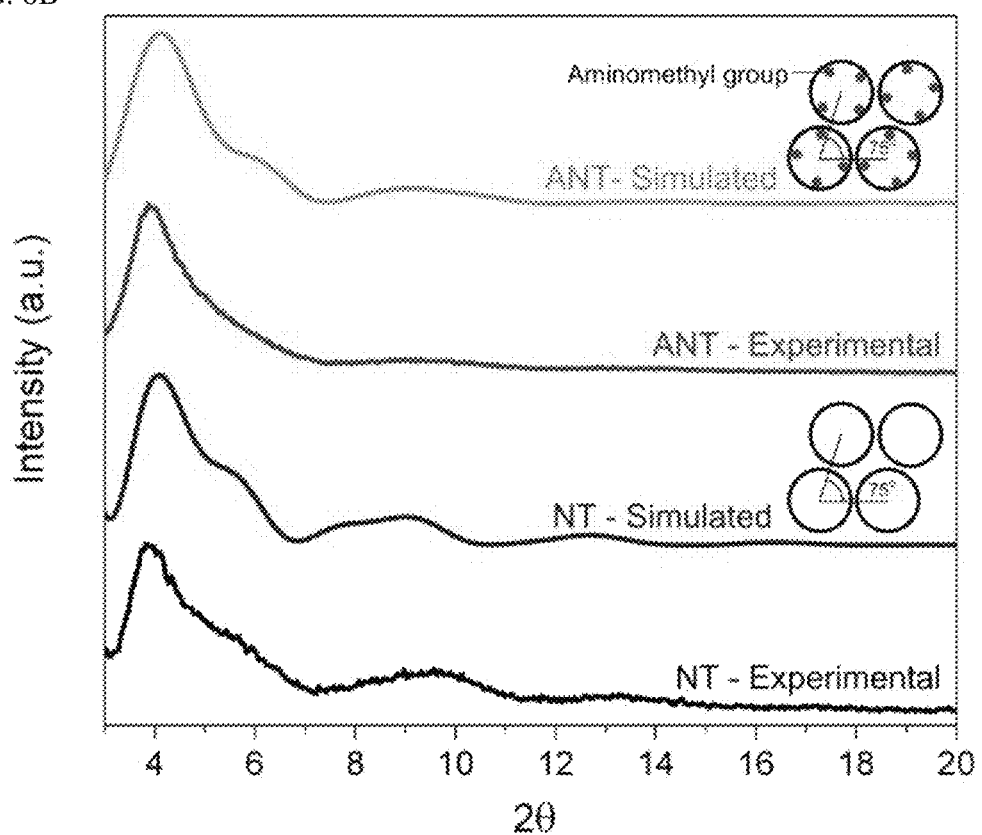
FIG. 6B illustrates a representative measured (experimental) and simulated X-ray diffraction (XRD) patterns of SWNTs, in which the top two are prepared in accordance with a method associated with FIG. 1B and the bottom two are prepared in accordance with a method associated with FIG. 1A.

FIG. 6B. The XRD patterns for NTs were not dominated by Bragg diffraction but by scattering from small bundles of NTs (see e.g., Kang, D.-Y., et al., *ACS Nano*, 4 (2010) 4897; Kang, D.-Y., et al., *ACS Appl. Mater. Interfaces*, 4 (2012) 965). Both computational and experimental evidence showed that NTs formed small bundles of three or four individual nanotubes. In ANTs, immobilization of the functional units (e.g., aminomethyl groups) at the inner surface of the nanotubes caused a slight deviation in the form factor (bundle of three or four nanotubes) that differed from the form factor of the bare nanotubes. ANTs showed an ideal core-shell cylindrical object with uniform scattering length density. This difference between NTs and ANTs was captured successfully in both experimental and simulated XRD patterns, wherein the ANTs showed less prominent features in the regions of 5-6°, 8-10°, and 12-14° 2θ. This demonstrates the successful synthesis of ANTs. In the example, nanotube synthesis with 20% compatible organic compound (AMTES) substitution for the condensable precursor (TEOS) successfully yielded ANTs with 15% $T^3(6Al)$ substitution for $Q^3(6Al)$ in the nanotube wall, hence 15% functionalization along the surface of the inner pore wall.

The functionality of the ANT material was evaluated using single-component gas adsorption measurements via quartz crystal microbalance (QCM)-based gravimetric techniques developed by the inventors (see e.g., Venkatasubramanian, A., et al., *J. Phys. Chem. C*, 116 (2012) 15313). For sample preparation, the as-synthesized NT or ANT gel was drop-coated (depositing a few drops on the QCM substrate, followed by baking in an oven at 110° C. and atmospheric pressure for 30 minutes). Samples were mounted in the apparatus and degassed in situ at a temperature of 180° C. under a vacuum of 20 Torr for about 24 hours before adsorption measurements. Single-component adsorption isotherms of $CO_2$, $CH_4$, and $N_2$ in the nanotubes were then collected at 25° C. and 67° C. at pressures ranging from 0.3-120 psi (about 8 atm). Measurements were taken in pressure intervals of 2-3 psi (below 1 atm) and ~40 psi (above 1 atm). The choice of the functional units determined the molecular pairs that were assessed. With aminomethyl groups, $CO_2/N_2$ and $CO_2/CH_4$ molecular pairs were evaluated to assess their effect on adsorptive selectivity for $CO_2$, which is relevant to flue gas and natural gas purification.

Figure 7A:
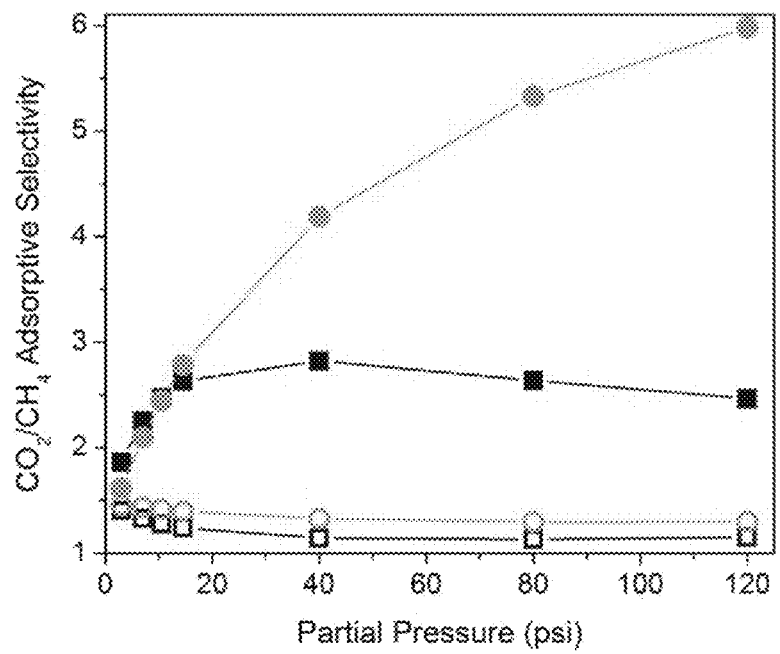
FIG. 7A illustrates a representative ideal $CO_2$ adsorption selectivity of SWNTs prepared in accordance with a method associated with FIG. 1A (open symbols) or in accordance with a method associated with FIG. 1B (closed symbols) for gas pairs of $CO_2/CH_4$ at 25° C. (squares) and at 67° C. (circles)
Figure 7B:
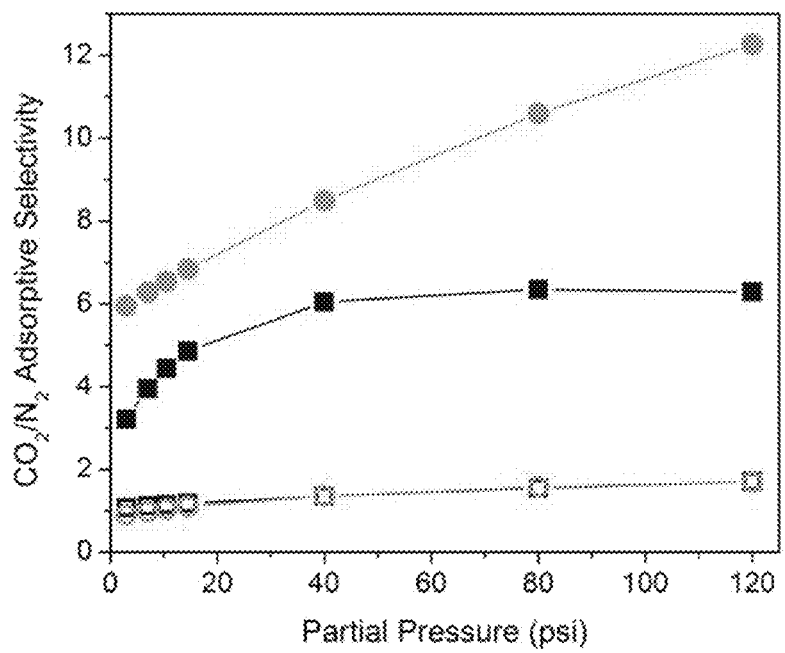
FIG. 7B illustrates a representative ideal $CO_2$ adsorption selectivity of SWNTs prepared in accordance with a method associated with FIG. 1A (open symbols) or in accordance with a method associated with FIG. 1B (closed symbols) for gas pairs of $CO_2/N_2$ at 25° C. (squares) and at 67° C. (circles)

FIG. 7 illustrates the ideal adsorption selectivity of the exemplary NTs and ANTs. FIGS. 12A-12F illustrate the full adsorption isotherms. The exemplary ANTs with a 15% functional unit substitution for hydroxyl groups, in which the functional unit was an aminomethyl group, exhibited a dramatic improvement in selectivity over the nonfunctionalized NTs for both $CO_2/CH_4$ (up to four-fold increase) and $CO_2/N_2$ (up to ten-fold increase). The Henry's constants for adsorption in each nanotube material were deduced from fits of the full isotherms to the Langmuir model. This evaluated the affinity of the ANT and NT walls for the adsorbate molecules. The Henry's constant ratios between ANTs and NTs$_{(K_{ANT}/K_{NT})}$ are summarized in TABLE 4.

TABLE 4

| Temperature | $CO_2$ | $CH_4$ | $N_2$ |
|---|---|---|---|
| 25° C. | 0.41 | 0.18 | 0.08 |
| 67° C. | 0.36 | 0.34 | 0.07 |

Figure 14:
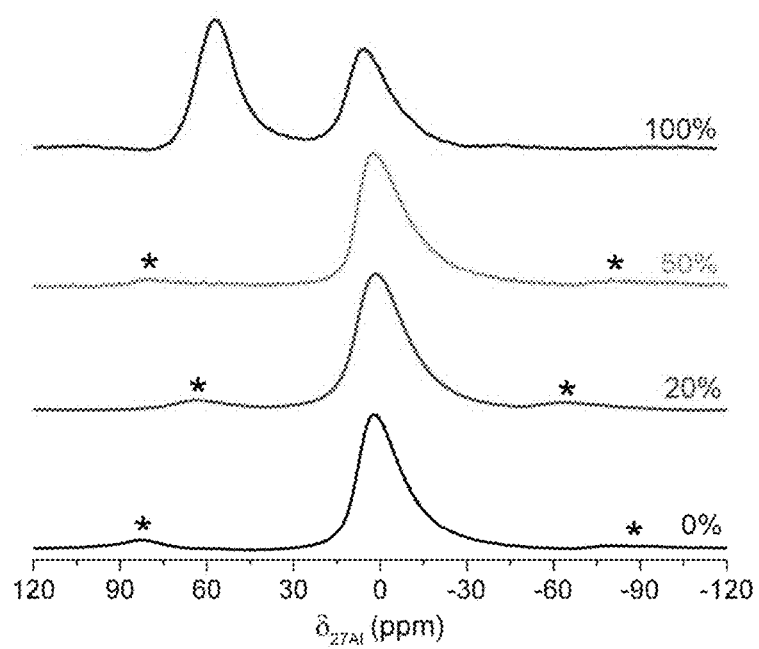
FIG. 14 illustrates $^{27}Al$ NMR spectra of the synthetic products from 0%, 20%, 50%, and 100% substitution of a compatible organic compound for a precursor during synthesis, in which a single octahedral aluminum peak is observed for up to 50% substitution and an additional tetrahydral aluminum peak (60 ppm) appears with 100% substitution.

Detailed Langmuir fitting parameters are presented in TABLE 5 and FIG. 14.

TABLE 5

| | | $CO_2$ | | $CH_4$ | | $N_2$ | |
|---|---|---|---|---|---|---|---|
| | | 25° C. | 67° C. | 25° C. | 67° C. | 25° C. | 67° C. |
| NT | $C_t$ (cm³/g STP) | 28.7 | 25.4 | 26.8 | 20.9 | 14.4 | 11.5 |
| | α (1/psi) | 0.02 | 0.014 | 0.018 | 0.012 | 0.048 | 0.037 |
| ANT | $C_t$ (cm³/g STP) | 21.4 | 16.46 | 9.5 | 1.42 | 2.6 | 0.76 |
| | α (1/psi) | 0.011 | 0.0078 | 0.0089 | 0.06 | 0.022 | 0.038 |

In general, the Henry's constants decreased for all adsorbates when partially replacing surface hydroxyl groups with the exemplary functional units, the aminomethyl groups, suggesting that the isolated functional units ($\equiv$Si—$CH_2NH_2$) in the ANTs possessed a weaker affinity for the adsorbates in comparison to the hydroxyls groups ($\equiv$Si—OH). The Henry's constant reduction is much more significant for $CH_4$ and $N_2$ than for $CO_2$, and provides the main contribution to the enhanced $CO_2/CH_4$ and $CO_2/N_2$ selectivity. The smaller reduction of Henry's constant for $CO_2$ is likely due to amine group binding to $CO_2$ molecules. Specifically, previous studies have shown that one equivalent of a free base moiety, typically water, is needed for a primary amine to adsorb one equivalent of $CO_2$ (see e.g., Choi, S., et al., *ChemSusChem*, 2 (2009) 796; Bollini, P., et al., *J. Mater. Chem.*, 21 (2011) 15100). Under anhydrous conditions with the adsorption measurements used on the exemplary nanotubes, two adjacent primary amines were required to adsorb one equivalent of $CO_2$.

In the exemplary functionalized nanotubes, primary amine groups are expected to be distributed in a random manner at the inner surface of the ANTs; there is no evidence showing preferred clustering of the aminomethlysilane groups. Given the adsorption mechanism discussed above, amine groups that have a second amine group nearby, immobilized on a concaved surface with high degree of curvature, may provide a positive contribution to $CO_2$ adsorption, whereas the isolated amines would likely show lower $CO_2$ affinity than the surface hydroxyls. These two competing effects, present only for $CO_2$ adsorption but not for $CH_4$ and $N_2$, are likely to be the key factor leading to a relatively small reduction of Henry's constant for $CO_2$ and the high $CO_2/CH_4$ and $CO_2/N_2$ selectivity in ANTs.

Direct Synthesis of Other Functionalized Single-Walled Nanotube Compositions

Described then is a single-step approach for synthesis and fabrication of single-walled nanotubes (ANTs) with a 15% functional unit substitution for the hydroxyl groups on the interior nanotube wall. While the exemplary embodiment included aluminosilicate nanotubes functionalized during synthesis with aminomethyl groups, other functionalized single walled metal oxide nanotubes may also be prepared by the methods described herein. Said functionalized single walled metal oxide nanotubes will have altered interior surface properties with functionalization localized throughout the interior of the inner pore wall surface. For example, the direct functionalization strategy described herein provides a means for using nanotubes in separations and catalysis applications, based on the existence of the functional groups and also allows further chemical modifications thereof by additional substitution reactions. This is represented by the fact that ANTs as described herein, in which the nanotubes were synthetically modified during synthesis by the incorporation of primary amines, showed a substantial increase or enhanced in $CO_2/CH_4$ and $CO_2/N_2$ adsorption selectivity in the interior pore as compared to the nonfunctionalized NTs. As such, the compositions and methods described herein provide new approaches that enable a wider range of applications for nanotubes, which have so far been inaccessible to other nanotube systems.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims.

Definitions

As used herein, the terms "a," "an," "the," and "said" when used in conjunction with the term "comprising" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject.

As used herein, the phrase "consisting essentially of" occupies a middle ground, allowing the addition of non-material elements that do not substantially change the nature of the invention, such as various buffers, differing salts, extra wash or precipitation steps, pH modifiers, and the like.

As used herein, the term "simultaneously" means occurring at the same time or about the same time, including concurrently.

Abbreviations

The following abbreviations are used herein:

| | |
|---|---|
| CNT | Carbon nanotubes |
| SWNT | Single-walled nanotubes |
| TEOS | Tetraethyl orthosilicate |
| AMTES | Aminomethyltriethoxysilane |
| NT | Synthesized nonfunctionalized, bare nanotube |
| ANT | Nanotube functionalized during synthesis |
| TEM | Transmission electronic microscopy |
| cryo-EM | cryo-electron microscopy |
| ED | Electron diffraction |
| DP | Direct polarization |
| CP | Cross polarization |
| NMR | Nuclear magnetic resonance |
| FT | Fourier transform |
| TRAPDOR | Transfer of Populations in Double Resonance |
| XRD | X-ray diffraction |
| QCM | Quartz crystal microbalance |

INCORPORATION BY REFERENCE

All patents and patent applications, articles, reports, and other documents cited herein are fully incorporated by reference to the extent they are not inconsistent with this invention, as follows:

(1) Iijima, S. *Nature,* 354 (1991) 56.
(2) Ma, P. C.; Siddiqui, N. A.; Marom, G.; Kim, J. K. *Composite Part A,* 41 (2010) 1345.
(3) Singh, P.; Campidelli, S.; Giordani, S.; Bonifazi, D.; Bianco, A.; Prato, M. *Chem. Soc. Rev.,* 38 (2009) 2214.
(4) Karousis, N.; Tagmatarchis, N.; Tasis, D. *Chem. Rev.,* 110 (2010) 5366.
(5) Kuzmany, H.; Kukovecz, A.; Simon, F.; Holzweber, A.; Kramberger, C.; Pichler, T. *Synth. Met.,* 141 (2004) 113.
(6) Vairavapandian, D.; Vichchulada, P.; Lay, M. D. *Anal. Chim. Acta,* 626 (2008) 119.
(7) Singh, S.; Kruse, P. *Int. J. Nanotechnol.,* 5 (2008) 900.
(8) Yanagi, K.; Iakoubovskii, K.; Matsui, H.; Matsuzaki, H.; Okamoto, H.; Miyata, Y.; Maniwa, Y.; Kazaoui, S.; Minami, N.; Kataura, H. *J. Am. Chem. Soc.,* 129 (2007) 4992.
(9) Majumder, M.; Chopra, N.; Hinds, B. J. *ACS Nano,* 5 (2011) 3867.
(10) Giambastiani, G.; Cicchi, S.; Giannasi, A.; Luconi, L.; Rossin, A.; Mercuri, F.; Bianchini, C.; Brandi, A.; Melucci, M.; Ghini, G.; Stagnaro, P.; Conzatti, L.; Passaglia, E.; Zoppi, M.; Montini, T.; Fornasiero, P. *Chem. Mater.,* 23 (2011) 1923.
(11) Wada, S. I.; Eto, A.; Wada, K. *J. Soil Sci.,* 30 (1979) 347.
(12) Barron, P. F.; Wilson, M. A.; Campbell, A. S.; Frost, R. L. *Nature,* 299 (1982) 616.
(13) Mukherjee, S.; Bartlow, V. A.; Nair, S. *Chem. Mater.,* 17 (2005) 4900.
(14) Kang, D.-Y.; Zang, J.; Wright, E. R.; McCanna, A. L.; Jones, C. W.; Nair, S. *ACS Nano,* 4 (2010) 4897.
(15) Theng, B. K. G.; Russell, M.; Churchman, G. J.; Parfitt, R. L. *Clays Clay Miner.,* 30 (1982) 143.
(16) Mukherjee, S.; Kim, K.; Nair, S. *J. Am. Chem. Soc.,* 129 (2007) 6820.
(17) Levard, C.; Rose, J.; Thill, A.; Masion, A.; Doelsch, E.; Maillet, P.; Spalla, O.; Olivi, L.; Cognigni, A.; Ziarelli, F.; Bottero, J. Y. *Chem. Mater.,* 22 (2010) 2466.
(18) Maillet, P.; Levard, C.; Spalla, 0.; Masion, A.; Rose, J.; Thill, A. *Phys. Chem. Chem. Phys.,* 13 (2011) 2682.
(19) Yucelen, G. I.; Choudhury, R. P.; Vyalikh, A.; Scheler, U.; Beckham, H. W.; Nair, S. *J. Am. Chem. Soc.,* 133 (2011) 5397.

(20) Yucelen, G. I.; Kang, D.-Y.; Guerrero-Ferreira, R. C.; Wright, E. R.; Beckham, H. W.; Nair, S. *Nano Lett.*, 12 (2012) 827.
(21) Bottero, I.; Bonelli, B.; Ashbrook, S. E.; Wright, P. A.; Zhou, W.; Tagliabue, M.; Armandi, M.; Garrone, E. *Phys. Chem. Chem. Phys.*, 13 (2011) 744.
(22) Kang, D. Y.; Zang, J.; Jones, C. W.; Nair, S. *J. Phys. Chem. C*, 115 (2011) 7676.
(23) Zanzottera, C.; Vicente, A.; Celasco, E.; Fernandez, C.; Garrone, E.; Bonelli, B. *J Phys. Chem. C*, 116 (2012) 7499.
(24) Jones, C. W.; Tsuji, K.; Davis, M. E. *Nature*, 393 (1998) 52.
(25) Tsuji, K.; Jones, C. W.; Davis, M. E. *Microporous Mesoporous Mater.*, 29 (1999) 339.
(26) Jones, C. W.; Tsuji, K.; Davis, M. E. *Microporous Mesoporous Mater.*, 33 (1999) 223.
(27) Stein, A.; Melde, B. J.; Schroden, R. C. *Adv. Mater.*, 12 (2000) 1403.
(28) Hoffmann, F.; Cornelius, M.; Morell, J.; Froba, M. *Angew. Chem. Int. Ed.*, 45 (2006) 3216.
(29) Brunelli, N. A.; Didas, S. A.; Venkatasubbaiah, K.; Jones, C. W. *J. Am. Chem. Soc.*, 134 (2012) 13950.
(30) Grey, C. P.; Vega, A. J. *J. Am. Chem. Soc.*, 117 (1995) 8232.
(31) Venkatasubramanian, A.; Navaei, M.; Bagnall, K. R.; McCarley, K. C.; Nair, S.; Hesketh, P. J. *J. Phys. Chem. C*, 116 (2012) 15313.
(32) Ek, S.; Iiskola, E. I.; Niinisto, L.; Vaittinen, J.; Pakkanen, T. T.; Root, A. *J. Phys. Chem. B*, 108 (2004) 11454.
(33) Socrates, G., INFRARED AND RAMAN CHARACTERISTIC GROUP FREQUENCIES: TABLES AND CHARTS (Wiley, Chichester ed., 3d ed., 2001).
(34) Holland, G. P.; Alam, T. M. *Phys. Chem. Chem. Phys.*, 7 (2005) 1739.
(35) Kang, D.-Y.; Tong, H. M.; Zang, J.; Choudhury, R. P.; Sholl, D. S.; Beckham, H. W.; Jones, C. W.; Nair, S. *ACS Appl. Mater. Interfaces*, 4 (2012) 965.
(36) Cambedouzou, J.; Pichot, V.; Rols, S.; Launois, P.; Petit, P.; Klement, R.; Kataura, H.; Almairac, R. *Eur. Phys. J. B*, 42 (2004) 31.
(37) Tagliabue, M.; Farrusseng, D.; Valencia, S.; Aguado, S.; Rayon, U.; Rizzo, C.; Corma, A.; Mirodatos, C. *Chem. Eng. J.*, 155 (2009) 553.
(38) Bollini, P.; Choi, S.; Drese, J. H.; Jones, C. W. *Energy Fuels*, 25 (2011) 2416.
(39) Choi, S.; Drese, J. H.; Jones, C. W. *ChemSusChem*, 2 (2009) 796.
(40) Bollini, P.; Didas, S. A.; Jones, C. W. *J. Mater. Chem.*, 21 (2011) 15100.

What is claimed is:

1. A functionalized single-walled metal-oxide nanotube comprising:
a metal-oxide nanotube having a single wall and opposing ends; and
a quantity of organic functional units incorporated on the inner surface of the single wall;
wherein the organic functional units are covalently bound to the inner surface of the single wall;
wherein the organic functional units are substituted for hydroxyl units on the inner surface of the single wall;
wherein the organic functional units bind to a component of the single wall, the component consisting of a Group IVA element; and
wherein the organic functional units are incorporated at various locations along a length of the inner surface of the single wall and wherein the organic functional units are not localized at one or more of the opposing ends of the single wall.

2. The functionalized single-walled metal-oxide nanotube of claim 1, wherein the Group IVA element is selected from silicon, germanium, tin and lead.

3. The functionalized single-walled metal-oxide nanotube of claim 2, wherein the metal-oxide nanotube is an aluminosilicate nanotube.

4. The functionalized single-walled metal-oxide nanotube of claim 2, wherein the organic functional units contain amino groups.

5. The functionalized single-walled metal-oxide nanotube eampositien of claim 2, wherein the quantity of organic functional units is at least about 15%.

6. The functionalized single-walled metal-oxide nanotube of claim 2, wherein the organic functional units are dispersed uniformly at the various locations along the length of the inner surface of the single wall.

7. The functionalized single-walled metal-oxide nanotube of claim 2, wherein the organic functional units do not impart hydrophobicity to the inner surface of the single wall.

8. The functionalized single-walled metal-oxide nanotube of claim 3, wherein the quantity of organic functional units is about 15%.

9. The functionalized single-walled metal-oxide nanotube of claim 2, wherein the organic functional units include organic functional units that are not sterically capable of being incorporated along a length of the inner surface of the single-wall were the organic functional units to be incorporated after synthesis of the metal-oxide nanotube.

10. The functionalized single-walled metal-oxide nanotube of claim 2, wherein the organic functional units are incorporated on the inner surface of the single wall during synthesis of metal-oxide nanotubes.

11. A method of preparing a functionalized single-walled metal-oxide nanotube of claim 1 comprising the steps of:
combining as an aqueous reaction mixture a condensable precursor containing a Group IV element, an organic compound containing an organic functional unit bonded to a Group IV element, and an oxidizing agent containing a metallic material;
wherein when the condensable precursor has a general structure of X—$R_n$, the organic compound has a general structure of R'—X—$R_{n-1}$ and when the condensable precursor has a general structure of X—$(OR)_n$, the organic compound has a general structure of R'—X—$(OR)_{n-1}$, wherein X is a Group IVA element selected from silicon, germanium, tin and lead, wherein X is the same element in both the condensable precursor and the organic compound, wherein R' is the organic functional unit selected from hydrogen, alkyl, aryl, amino, epoxy, sulfido, vinyl, methacrylic, mercapto, isocyanate or other organofunctional group and combinations thereof, wherein OR is any of a methoxy, ethoxy, propoxy or acetoxy group and combinations thereof, and wherein n=1,2,3 or 4; and
allowing the aqueous reaction mixture to undergo a reaction.

12. The method of claim 11, wherein the condensable precursor and the organic compound are in a ratio of (1−x) to (x).

13. The method of claim 11 wherein combining comprises mixing the aqueous reaction mixture initially under nitrogen followed by addition of a strong acid and stirring vigorously at an ambient temperature.

14. The method of claim 13, wherein the reaction is allowed to proceed for about 24 hours.

15. The method of claim 11 further comprising a step of forming a gel after the reaction.

16. The method of claim 15 further comprising a step of treating the gel to obtain a powder.

17. The method of claim 11 where the reaction includes condensing the aqueous reaction mixture at a temperature less than 100° C.

18. The method of claim 11, wherein the aqueous reaction mixture further comprises an acid.

19. The method of claim 18, wherein the ratio of the condensable precursor to the organic compound to the acid is $(1-x):(x):1$.

20. The method of claim 18, wherein the ratio of the condensable precursor to the organic compound to the metallic material to the acid is $(1-x):(x):2:1$.

* * * * *